(12) United States Patent
Lennartsson et al.

(10) Patent No.: US 9,994,872 B2
(45) Date of Patent: Jun. 12, 2018

(54) INTEGRATION OF FIRST AND SECOND GENERATION BIOETHANOL PROCESSES

(71) Applicant: LANTMÄNNEN ENERGI, Stockholm (SE)

(72) Inventors: Patrik R. Lennartsson, Borås (SE); Per Erlandsson, Stockholm (SE); Mohammad Taherzadeh, Borås (SE); Andreas Gundberg, Norrköping (SE)

(73) Assignee: LANTMÄNNEN ENERGI, Stockholm (SE)

( * ) Notice: Subject to any disclaimer, the term of this patent is extended or adjusted under 35 U.S.C. 154(b) by 0 days. days.

(21) Appl. No.: 15/103,935

(22) PCT Filed: Dec. 12, 2014

(86) PCT No.: PCT/EP2014/077521
§ 371 (c)(1),
(2) Date: Jun. 13, 2016

(87) PCT Pub. No.: WO2015/086803
PCT Pub. Date: Jun. 18, 2015

(65) Prior Publication Data
US 2016/0312247 A1    Oct. 27, 2016

(30) Foreign Application Priority Data
Dec. 13, 2013 (SE) ...................... 1351496

(51) Int. Cl.
*C12P 7/14* (2006.01)
*C12P 7/06* (2006.01)
*C12P 7/10* (2006.01)
*C08H 8/00* (2010.01)
*A23K 10/12* (2016.01)
*A23K 10/38* (2016.01)
*A23K 50/80* (2016.01)
*A23L 33/12* (2016.01)
*A23L 33/195* (2016.01)
*A23L 7/104* (2016.01)
*A23L 7/10* (2016.01)

(52) U.S. Cl.
CPC ............ *C12P 7/065* (2013.01); *A23K 10/12* (2016.05); *A23K 10/38* (2016.05); *A23K 50/80* (2016.05); *A23L 7/104* (2016.08); *A23L 7/198* (2016.08); *A23L 33/12* (2016.08); *A23L 33/195* (2016.08); *C08H 8/00* (2013.01); *C12P 7/10* (2013.01); *C12P 2203/00* (2013.01); *Y02A 40/818* (2018.01); *Y02E 50/16* (2013.01); *Y02E 50/17* (2013.01); *Y02P 60/873* (2015.11)

(58) Field of Classification Search
None
See application file for complete search history.

(56) References Cited

U.S. PATENT DOCUMENTS

| | | | | |
|---|---|---|---|---|
| 8,431,755 | B2 * | 4/2013 | Vauk | C01B 3/34 44/605 |
| 8,481,295 | B2 * | 7/2013 | van Leeuwen | C02F 3/34 435/171 |
| 2010/0196994 | A1 * | 8/2010 | van Leeuwen | C12N 1/14 435/256.1 |
| 2013/0143277 | A1 * | 6/2013 | Gutierrez | C12N 1/22 435/99 |
| 2014/0329292 | A1 * | 11/2014 | Emarlfarb | C07H 21/00 435/198 |
| 2015/0004672 | A1 * | 1/2015 | de Crecy, Jr. | C12P 7/6463 435/245 |

OTHER PUBLICATIONS

Dogaris, I. et al. Biotechnological Production of Ethanol from Renewable Resources . . . Applied Microbiology and Biotechnology 97(4)1457-1473, Feb. 2013.*
Millati R. et al. Performance of Rhizopus, Rhizomucor, and Mucor in Ethanol Production from Glucose, Xylose, and Wood Hydrolyzates. Enzyme and Microbial Technology 36(2-3)294-300, 2005.*
Wikandari R. et al. Isolation and Characterization of Zygomycetes Fungi from Tempe for Ethanol Production and Biomass Applications. Applied Biochemistry Biotechnology 167:1501-1512, 2012.*
Dias M. et al. Improving Second Generation Ethanol Production Through Optimization of First Generation Production Process from Sugarcane. Energy 43:246-252, 2012.*

* cited by examiner

*Primary Examiner* — Ralph J Gitomer
(74) *Attorney, Agent, or Firm* — Cermak Nakajima & McGowan LLP; Malcolm K. McGowan

(57) ABSTRACT

The present invention presents an alternative to the direct implementation of an industrial scale second generation bioethanol process with the integration of the second generation into the existing first generation bioethanol processes, which aims to reduce the current barriers to process change/investments. In particular, the present invention relates to an integrated second generation process for producing bioethanol comprising at least one fungal cultivation stage for producing ethanol and fungal biomass. The present invention also relates to a novel fungal biomass, rich in protein and essential amino acids, which is produced with said integrated second generation process for producing bioethanol for use as a nutritious substitute for human and domestic animal use.

12 Claims, 27 Drawing Sheets

Table 1

| | A. oryzae | F. venenatum | M. purpureus | N. intermedia |
|---|---|---|---|---|
| Fungal Biomass | | | | |
| Biomass dry weight (g/L) | 19 ± 1 | 14 ± 1 | 12 ± 2 | 16 ± 2 |
| % Crude protein (g/g) | 48 ± 0 | 56 ± 0 | 44 ± 2 | 56 ± 3 |
| AIM (mg/g) | ND* | ND | ND | ND |
| GlcN (mg/g) | ND | ND | ND | ND |
| GlcNAc (mg/g) | ND | ND | ND | ND |
| Spent Thin Stillage | | | | |
| pH | 6.0 ± 0.0 | 5.4 ± 0.1 | 5.5 ± 0.1 | 6.0 ± 0.1 |
| Lactic acid reduction (%) | 0 | 0 | 0 | 0 |
| Glycerol reduction (%) | 54 ± 0 | 14 ± 2 | 7 ± 1 | 10 ± 3 |
| Ethanol (g/L) | 1.7 ± 0.2 | 2.4 ± 0.3 | 1.9 ± 0.1 | 5.5 ± 0.1 |
| Xylose (g/L) | 1.1 ± 0.1 | 1.0 ± 0.0 | 1.2 ± 0.0 | 0.3 ± 0.1 |
| Arabinose (g/L) | 1.2 ± 0.1 | 2.0 ± 0.0 | 0.6 ± 0.1 | 1.5 ± 0.4 |
| TS reduction (%)** | 32 ± 1 | 21 ± 3 | 16 ± 5 | 34 ± 9 |
| SS reduction (%)*** | 55 ± 6 | 40 ± 1 | 58 ± 4 | 69 ± 20 |

Fig. 6

Table 2

| Component (mg/g) | DDGS* | N. intermedia | Component (mg/g) | DDGS | N. intermedia |
|---|---|---|---|---|---|
| Protein content and amino acid profile | | | Lipid content and fatty acid profile | | |
| KN | 51.4 ± 1.3 | 529 ± 65 | Lipid | 77 ± 2 | 116 ± 11 |
| Alanine | 20.2 ± 0.5 | 32 ± 4 | C 14:0 | ND** | < 1 |
| Ammonia | 17.2 ± 0.4 | 13 ± 3 | C 15:0 | ND | < 1 |
| Arginine | 23.1 ± 0.6 | 29 ± 8 | C 16:0 | ND | 24 ± 5 |
| Aspartic | 28.6 ± 0.7 | 39 ± 9 | C 16:1 n-7 | ND | < 1 |
| Cysteine | 11.1 ± 0.3 | 6 ± 1 | C 17:0 | ND | < 1 |
| Glutamic acid | 143.2 ± 3.6 | 52 ± 10 | C 17:1 n-7 | ND | < 1 |
| Glycine | 19.3 ± 0.5 | 22 ± 6 | C 18:0 | ND | 4 ± 0 |
| Histidine | 11.2 ± 0.3 | 12 ± 3 | C 18:1 n-9 | ND | 18 ± 1 |
| Isoleucine | 21.8 ± 0.6 | 21 ± 7 | C 18:2 n-6 | ND | 55 ± 4 |
| Leucine | 37.7 ± 1.0 | 32 ± 10 | C 18:3 n-3 | ND | 5 ± 0 |
| Lysine | 15.7 ± 0.4 | 33 ± 9 | C 20:0 | ND | < 1 |
| Metionine | 8.4 ± 0.2 | 8 ± 3 | C 20:1 n-9 | ND | < 1 |
| Ornitine | 0.3 ± 0.0 | 6 ± 1 | C 20:2 n-6 | ND | < 1 |
| Proline | 46.0 ± 1.2 | 19 ± 3 | C 22:0 | ND | < 1 |
| Phenylalaline | 25.2 ± 0.6 | 18 ± 6 | C 24:0 | ND | < 1 |
| Serine | 26.2 ± 0.7 | 21 ± 5 | C 24:1 n-9 | ND | < 1 |
| Threonine | 16.8 ± 0.4 | 21 ± 5 | | | |
| Tryptophan | 5.7 ± 0.1 | 7 ± 2 | | | |
| Tyrosine | 18.1 ± 0.5 | 15 ± 4 | | | |
| Valine | 26.1 ± 0.7 | 27 ± 9 | | | |

Fig. 7

Table 3

| Parameter | Batch | Continuous |
|---|---|---|
| pH | 3.5 ± 0.0 | 4.3 ± 0.0 |
| Kjeldahl nitrogen (g/L) | 4.4 ± 0.2 | 5.3 ± 0.1 |
| Total solids (g/L) | 77.5 ± 3.4 | 90.1 ± 3.3 |
| Suspended solids (g/L) | 26.0 ± 0.9 | 30.5 ± 0.2 |
| Ash (g/L) | 10.3 ± 0.5 | 8.8 ± 0.4 |
| *Dissolved monomers* | | |
| Arabinose (g/L) | 0.6 ± 0.1 | 1.0 ± 0.1 |
| Galactose (g/L) | ND$^c$ | 0.7 ± 0.1 |
| Glucose (g/L) | 0.5 ± 0.1 | 0.9 ± 0.1 |
| Xylose (g/L) | 0.6 ± 0.2 | 0.7 ± 0.1 |
| Glycerol (g/L) | 7.6 ± 0.5 | 9.9 ± 0.1 |
| Acetic acid (g/L) | 0.9 ± 0.1 | 0.3 ± 0.1 |
| Ethanol (g/L) | 1.7 ± 0.2 | 0.4 ± 0.1 |
| Lactic acid (g/L) | 11.6 ± 0.9 | 2.8 ± 0.1 |
| *Dissolved oligomers* | | |
| Arabinose (g/L) | 4.4 ± 0.2 | 6.2 ± 0.0 |
| Galactose (g/L) | 1.6 ± 0.2 | 1.7 ± 0.0 |
| Glucose (g/L) | 9.8 ± 0.7 | 16.4 ± 0.3 |
| Mannose (g/L) | 1.4 ± 0.2 | 1.7 ± 0.2 |
| Xylose (g/L) | 6.1 ± 0.4 | 6.8 ± 0.1 |
| *Solid fraction* | | |
| Arabinan (mg/L) | 242 ± 140 | 374 ± 46 |
| Galactan (mg/L) | 175 ± 42 | 193 ± 32 |
| Glucan (mg/L) | 3182 ± 383 | 4553 ± 531 |
| Mannan (mg/L) | 488 ± 234 | 979 ± 83 |
| Xylan (mg/L) | 907 ± 419 | 920 ± 129 |

Fig. 9

Table 4:

| Component (mg/g) | DDGS* | N. intermedia | Component (mg/g) | DDGS | N. intermedia |
|---|---|---|---|---|---|
| Protein content and amino acid profile | | | Lipid content and fatty acid profile | | |
| KN | 51.4 ± 1.3 | 529 ± 65 | Lipid | 77 ± 2 | 116 ± 11 |
| Alanine | 20.2 ± 0.5 | 32 ± 4 | C 14:0 | ND** | < 1 |
| Ammonia | 17.2 ± 0.4 | 13 ± 3 | C 15:0 | ND | < 1 |
| Arginine | 23.1 ± 0.6 | 29 ± 8 | C 16:0 | ND | 24 ± 5 |
| Aspartic | 28.6 ± 0.7 | 39 ± 9 | C 16:1 n-7 | ND | < 1 |
| Cysteine | 11.1 ± 0.3 | 6 ± 1 | C 17:0 | ND | < 1 |
| Glutamic acid | 143.2 ± 3.6 | 52 ± 10 | C 17:1 n-7 | ND | < 1 |
| Glycine | 19.3 ± 0.5 | 22 ± 6 | C 18:0 | ND | 4 ± 0 |
| Histidine | 11.2 ± 0.3 | 12 ± 3 | C 18:1 n-9 | ND | 18 ± 1 |
| Isoleucine | 21.8 ± 0.6 | 21 ± 7 | C 18:2 n-6 | ND | 55 ± 4 |
| Leucine | 37.7 ± 1.0 | 32 ± 10 | C 18:3 n-3 | ND | 5 ± 0 |
| Lysine | 15.7 ± 0.4 | 33 ± 9 | C 20:0 | ND | < 1 |
| Metionine | 8.4 ± 0.2 | 8 ± 3 | C 20:1 n-9 | ND | < 1 |
| Ornitine | 0.3 ± 0.0 | 6 ± 1 | C 20:2 n-6 | ND | < 1 |
| Proline | 46.0 ± 1.2 | 19 ± 3 | C 22:0 | ND | < 1 |
| Phenylalaline | 25.2 ± 0.6 | 18 ± 6 | C 24:0 | ND | < 1 |
| Serine | 26.2 ± 0.7 | 21 ± 5 | C 24:1 n-9 | ND | < 1 |
| Threonine | 16.8 ± 0.4 | 21 ± 5 | | | |
| Tryptophan | 5.7 ± 0.1 | 7 ± 2 | | | |
| Tyrosine | 18.1 ± 0.5 | 15 ± 4 | | | |
| Valine | 26.1 ± 0.7 | 27 ± 9 | | | |

Fig.10

| Analysis | Unit | as is | of dry substance |
|---|---|---|---|
| Alanine | g/kg | 4,6 | 33,6 |
| Ammonia | g/kg | 2,5 | 18,2 |
| Arginine | g/kg | 4,6 | 33,6 |
| Aspartic acid | g/kg | 5,7 | 41,6 |
| Cystine | g/kg | 1,3 | 9,5 |
| Phenylalanine | g/kg | 3,2 | 23,4 |
| Glutamic acid | g/kg | 14,2 | 103,6 |
| Glycine | g/kg | 3,3 | 24,1 |
| Histidine | g/kg | 1,9 | 13,9 |
| Hydroxiprolin | g/kg | 0 | 0,0 |
| Isoleucine | g/kg | 3,6 | 26,3 |
| Leucine | g/kg | 5,6 | 40,9 |
| Lysin | g/kg | 4,4 | 32,1 |
| Methionine | g/kg | 1,4 | 10,2 |
| Ornitine | g/kg | 0,9 | 6,6 |
| Proline | g/kg | 4,4 | 32,1 |
| Serin | g/kg | 3,5 | 25,5 |
| Threonine | g/kg | 3 | 21,9 |
| Tyrosine (calculated) | g/kg | 3 | 21,9 |
| Valine | g/kg | 4,5 | 32,8 |
| Tryptophane | g/kg | | 0,0 |
| Sum aa | g/kg | 73,3 | 535,0 |
| Crude protein N*6,25 ( Kjeldahl ) | % | 7,7 | 56,2 |
| Ash | % | 0,73 | 5,3 |
| Crude fat | % | 2,11 | 15,4 |
| Water | % | 86,3 | |
| Dry substance | % | 13,7 | 100,0 |
| Phosphorus | % | 0,18 | |
| Calcium | % | <0,02 | |
| K | % | 0,078 | |
| Na | % | <0,02 | |

Fig.17

INTEGRATION OF FIRST AND SECOND GENERATION BIOETHANOL PROCESSES

CROSS-REFERENCE TO RELATED APPLICATIONS

This application is a national stage application under 35 USC 371 of international application PCT/EP2014/077521, filed 12 Dec. 2014, which claims priority from Swedish application SE1351496-3, filed 13 Dec. 2013. The contents of these prior applications are incorporated herein in their entirety by reference

FIELD OF INVENTION

The present invention relates to the integration of a second generation process and the running dry mills e.g. from grains of a first generation processes for bioethanol production. In particular, the present invention relates to an integrated second generation process for producing bioethanol comprising at least one fungal cultivation stage for producing ethanol and fungal biomass.

The present invention also relates to a novel fungal biomass, rich in protein and essential amino acids, which is produced with said integrated second generation process for producing bioethanol, comprising at least one fungal cultivation stage, for use as a nutritious substitute for human and domestic animal use.

BACKGROUND OF THE INVENTION

Bioethanol is normally produced using yeast (*Saccharomyces cerevisiae*) to convert glucose into ethanol and carbon dioxide. Conversion of starch- or sugar-based raw materials into ethanol and carbon dioxide is often being referred to as the first generation process. When talking about the second generation process for bioethanol production, lignocellulose is one of a vast variety of possible choices for use as raw material (feed-stock). Lignocellulose consists of cellulose, hemicellulose and lignin and can be converted to glucose and pentoses using acid-, alkali-, and/or enzymatic pretreatment, or a combination of these. *S. cerevisiae* cannot convert pentoses to ethanol and therefore another kind of microorganism is needed to utilize the hemicellulose part of the raw material.

Some of the obstacles in the establishment of second generation bioethanol productions, are the investment costs and uncertainties in the process. One solution is to integrate the second generation process and the running dry mills of the first generation processes for ethanol production. However, the starch-based processes, which dominate the world market, are dependent on the by-products sold as animal feed, which make the process economically feasible. The quality of the animal feed therefore must not be negatively influenced by the integration. This also puts restraints on the method for utilizing the pentose sugars in the lignocellulosic substrate, as the microorganisms have to be food-grade. The proposed solution is to use food related filamentous Zygomycetes and Ascomycetes fungi, and to produce fungal biomass as a high-grade animal feed from the residues after the distillation (stillage). This also has the potential to improve the first generation process by increasing the amount of the thin stillage directly sent back into the process, and by decreasing the evaporator based problems.

From a human perspective, the world is dependent on fossil fuels for its primary energy supply. In 2010, we consumed 12.7 billion tons of oil equivalents globally, including 32.4% oil, 27.3% coal and peat, and 21.4% natural gas, while biofuels and waste contributed with 10.0%. Amongst the oil consumers, the transport sector completely dominated with 61.5% of the total consumption. Consequently, renewable alternatives for the transportation fuel should be seriously considered, if the fossil fuels are to be replaced.

During the last decade(s), concerns regarding global warming, fossil fuel depletion, and energy security resulted in a wide interest in renewable and environmentally friendly fuels. The dominating biofuel for transportation is ethanol with the annual world production rising from 17.0 to 86.1× $10^6$ m$^3$ from 2000 to 2011 (REN21, 2012). It is followed by biodiesel with an annual world production of 21.4×$10^6$ m$^3$ in 2011. The largest ethanol producing countries are U.S.A. and Brazil, responsible for the production of 54×$10^6$ and 21×$10^6$ m$^3$ in 2011, respectively (REN21, 2012). Currently, all industrial scale production of ethanol belongs to the first generation of biofuels. However, the technology to produce second generation ethanol does exist. One of the main obstacles for its implementation is the combination of high risk investments (including technological risks and political/policy risks) with low potential returns.

SUMMARY OF THE PRESENT INVENTION

The present invention presents an alternative to the direct implementation of an industrial scale second generation bioethanol process with the integration of the second generation into the existing first generation bioethanol processes, which aims to reduce the current barriers to process change/investments. The challenge of a pentose-rich substrate is also taken into account.

Thus, the present invention relates to an integrated second generation process for producing bioethanol comprising a second generation bioethanol process which is integrated into a first generation bioethanol process, characterized in that the integrated second generation process comprises at least one fungal cultivation stage and wherein the second generation process is (a) integrated at the fermentation stage, and/or (b) integrated at the fungal cultivation stage, and wherein the integrated second generation process produces ethanol and fungal biomass.

In one embodiment, the present invention relates to an integrated second generation process for producing bioethanol comprising at least one fungal cultivation stage, wherein the fungi introduced in the fungal cultivation stage are filamentous fungi. The filamentous fungi can be selected from the group consisting of food-related strains of Zygomycetes and Ascomycetes, such as *Rhizopus* sp.; *Fusarium venenatium; Aspergillus oryzae; Monascus purpureus, Neurospora intermedia* and combinations thereof.

A presently preferred embodiment of the present invention relates to an integrated second generation process for producing bioethanol comprising at least one fungal cultivation stage, wherein the filamentous fungi are selected from the group consisting of food-related strains of Zygomycetes.

An equally preferred embodiment of the present invention relates to an integrated second generation process for producing bioethanol comprising at least one fungal cultivation stage, wherein the filamentous fungi are selected from the group consisting of food-related strains of Ascomycetes, in particular, wherein the filamentous fungi are *Neurospora intermedia*.

Typically, the integrated second generation process for producing bioethanol according to the present invention yields an at least 1%, 2% or 2.5%, such as an at least 3%, 3.5%, 4%, 4.5%, 5%, 5.5%, 6%, 7%, 10% or 20% improvement of ethanol production compared to the ethanol production of the first generation bioethanol process into which the second generation bioethanol process is integrated.

In one embodiment, the invention relates to an integrated second generation process for producing bioethanol according to any of the preceding claims, wherein the integrated second generation process yields between 1-20%, such as between 1-2.5%, or between 2.5-5% improvement of ethanol production, compared to the ethanol production of the first generation bioethanol process into which the second generation bioethanol process is integrated.

An integrated second generation process for producing bioethanol according to the present invention typically yields and/or produces between 1-30 g/L fungal biomass, such as between 1-20, such as at least 5, 10, 15, 16, 17, 18, 19, or 20 g/L fungal biomass from the thin stillage.

An integrated second generation process for producing bioethanol according to the present invention typically yields and/or produces between 1-50 g/L additional ethanol, such as between 1-5, 5-10, 15-20, 35-50 g/L additional ethanol, or such as at least 1.5, 2, 2.5, 3, 3.5, 4, 4.5, 5, 5.5, 10, 15, 20, 25, 30, 35, 40, 45, 50 g/L additional ethanol from the thin stillage. In the present context, the term "additional ethanol" which is produced from the thin stillage is measured as the amount of ethanol produced in addition to or on top of the amount of ethanol that is typically or as a standard expected to be produced from the first generation process into which the second generation process is integrated, or which is actually produced by a similar and/or identical first generation process to the one into which the second generation process is integrated. The amount of ethanol that is typically or as a standard expected to be produced from the first generation process is of course dependent on the feed-stock and the individual process parameters employed and easily calculated by the person skilled in the field. The term is meant to be interchangeable with "surplus ethanol". To determine the potential volume of ethanol typically or as a standard produced per ton of various feed-stocks, the person skilled in the art knows to use commonly available database converters.

An integrated second generation process for producing bioethanol according to the present invention typically comprises a second generation process for producing bioethanol which is integrated into a first generation bioethanol process utilizing sugar(s) and/or starch. In a presently preferred embodiment, said second generation process for producing bioethanol is integrated into a first generation bioethanol process utilizing wheat.

An integrated second generation process for producing bioethanol according to the present invention typically comprises a second generation process for producing bioethanol which comprises ethanol production from pentose sugars released from e.g. lignocellulosic feed-stock selected from the group consisting of corn stover, wheat straw, switch grass, wheat bran, cellulose material, cellulose fibres, wood, barley straw, cassava straw, hemp, maize straw, oat straw, palm leafs, potato, rapeseed, rice, sorghum bicolor, soy, sugarcane, sugar beet, sunflower, yam, energy crops, *arundo*, big bluestem, camelina, chinese tallow, duckweed, jatropha curcas, millettia *pinnata, miscanthus giganteus*, wood fuel, and combinations thereof. In one embodiment, the lignocellulosic feed-stock is supplied at low concentrations. Typically, the lignocellulosic feed-stock is supplied into a dry mill.

In the present context, the terms lignocellulosic feedstock and/or lignocellulosic biomass are interchangeable and used to describe abundantly available raw material which is composed of carbohydrate polymers (cellulose, hemicellulose), and an aromatic polymer (lignin). These carbohydrate polymers contain different sugar monomers (six and five carbon sugars) and they are tightly bound to lignin. Lignocellulosic biomass can be broadly classified into virgin biomass, waste biomass and energy crops. Virgin biomass includes all naturally occurring terrestrial plants such as trees, bushes and grass. Waste biomass is produced as a low value byproduct of various industrial sectors such as agricultural (corn stover, sugarcane bagasse, straw etc.), forestry (saw mill and paper mill discards). Energy crops are crops with high yield of lignocellulosic biomass produced to serve as a raw material for production of second generation biofuel examples include switch grass (*Panicum virgatum*) and Elephant grass.

In one embodiment, the present invention relates to an integrated second generation process for producing bioethanol comprising at least one fungal cultivation stage, wherein the fungal cultivation step takes place in an airlift reactor and/or bubble column.

The present invention further relates to a fungal biomass produced by a process according to the present invention which can be either washed to remove residual yeast biomass and/or residual matter from the feed-stock, such as devitalized gluten proteins, solids and/or fibrous material, or "non-purified", as well as to a DDGS (distillers dried grains with solubles) comprising such a fungal biomass produced by a process according to the present invention. In particular, the present invention relates to a fungal biomass or a DDGS comprising said fungal biomass, wherein said fungal biomass is produced by an integrated second generation process for producing bioethanol comprising a second generation bioethanol process which is integrated into a first generation bioethanol process, characterized in that the integrated second generation process comprises at least one fungal cultivation stage and wherein the second generation process is (a) integrated at the fermentation stage, and/or (b) integrated at the fungal cultivation stage.

Typically, a fungal biomass or a DDGS according to the present invention is produced from the thin stillage of a starch-based first generation ethanol producing process.

A fungal biomass or a DDGS according to the present invention is rich in protein with an unusually favorable composition of amino acids. It typically has a crude protein content between 40-60% such as approximately 40, 41, 42, 43, 44, 45, 46, 47, 48, 49, 50, 51, 52, 53, 54, 55, 56, 57, 58, 59, or 60% (w/w). The crude protein content of the fungal biomass or DDGS can be at least 30, 35, 40, 45, 50, 55, or 60%.

Experiment 2 of the present invention discloses an analysis of a representative fungal biomass as well as a non-purified fungal biomass produced by an integrated second generation process for producing bioethanol comprising a second generation bioethanol process which is integrated into a first generation bioethanol process, characterized in that the integrated second generation process comprises at least one fungal cultivation stage and wherein the second generation process is (a) integrated at the fermentation stage, and/or (b) integrated at the fungal cultivation stage.

Accordingly, a representative non-purified fungal biomass according to the present invention comprises 45-55% (% of DS) protein, 5-20% (% of DS) fat, 2-5% (% of prot) lysine and 1-3% (% of prot) methionine.

A representative fungal biomass according to the present invention comprises 45-60% (% of DS) protein, 10-20% (% of DS) fat, 4-8% (% of prot) lysine and 1-4% (% of prot) methionine.

A fungal biomass according to the present invention typically comprises 5 g/L, such as between 3-7.5, 4-6 or 4.5-5.5 g/L, such as at least 3.5, 4, 4.5, 5, or 5.5 g/L fungal biomass, 5 g/L, such as between 3-7.5, 4-6 or 4.5-5.5 g/L before drying.

A non-purified fungal biomass according to the present invention typically comprises 5 g/L, such as between 3-7.5, 4-6 or 4.5-5.5 g/L, such as at least 3.5, 4, 4.5, 5, or 5.5 g/L fungal biomass, 5 g/L, such as between 3-7.5, 4-6 or 4.5-5.5 g/L, such as at least 3.5, 4, 4.5, 5, or 5.5 g/L yeast biomass and 15-25 g/L, such as between 13-17.5, 14-16, 18-20, 15-17 or 14.5-15.5 g/L, such as at least 13.5, 14, 14.5, 15, 15.5, 16, 16.5, 17, 17.5, 18, 18.5, 19, 19.5, 20, 21, 22, 23, 24 or 25 g/L residual mass from the feed-stock before drying. Purifying the fungal biomass comprises a variety of washing steps to separate the fungal biomass from at least parts of the yeast biomass and/or the residue from the feed-stock. Depending on the intended degree of purity of the fungal biomass, the person skilled in the art will know to employ different standard procedures.

The separated yeast biomass and/or the residue from the feed-stock can be used as nutritional substances on their own or in combination with each other. Consequently, the present invention also relates to yeast biomass produced by a process according to the present invention, as well as to residual mass from the feed-stock produced by a process according to the present invention.

A DDGS according to the present invention typically comprises 5 g/L, such as between 3-7.5, 4-6 or 4.5-5.5 g/L, such as at least 3.5, 4, 4.5, 5, or 5.5 g/L fungal biomass, 5 g/L, such as between 3-7.5, 4-6 or 4.5-5.5 g/L, such as at least 3.5, 4, 4.5, 5, or 5.5 g/L yeast biomass and 15-25 g/L, such as between 13-17.5, 14-16, 18-20, 15-17 or 14.5-15.5 g/L, such as at least 13.5, 14, 14.5, 15, 15.5, 16, 16.5, 17, 17.5, 18, 18.5, 19, 19.5, 20, 21, 22, 23, 24 or 25 g/L residual mass from the feed-stock mixed with solids before drying.

A fungal biomass or a DDGS according to the present invention contains vitamins, unsaturated 18 carbon fatty acid compounds and chitosan. In particular, a fungal biomass or a DDGS according to the present invention comprises essential amino acids, omega-3 and/or omega-6 fatty acids.

In one embodiment, the non-purified fungal biomass contains edible fungi (e.g. *Neurospora intermedia*), yeast, e.g. *Saccharomyces cerevisiae* (brewer's yeast) and devitalized gluten proteins from wheat. It has a high protein concentration with improved aminoacid profile compared to traditionally produced wheat based DDGS or CDS. It contains vitamins, such as B-vitamins, and biocomplexed minerals with improved digestibility.

Active substances in the products, such as Mannan-oligosaccharides and Beta-Glucans result in modulation of gut bacteria, stimulation of immune system and reduced risk of pathogen colonization to the gut wall. *Neurospora intermedia* is an edible fungi, which has long been used in Asia to produce fermented food, and can be used as probiotica.

The present invention relates to an integrated second generation process for producing bioethanol comprising at least one fungal cultivation stage, wherein the fungi introduced in the fungal cultivation stage are filamentous fungi selected from the group consisting of food-related strains of Zygomycetes and Ascomycetes, such as *Rhizopus* sp.; *Fusarium venenatium*; *Aspergillus oryzae*; *Monascus pureus, Neurospora intermedia* and combinations thereof. The whole cell-biomass can be killed and included into standard types of food, food supplement, or feed compositions. Therefore, the fungal biomass or a DDGS according to the present invention is well suited as a nutrient source for both humans and animals. The present invention thus discloses a nutrient source comprising fungal biomass or a DDGS according to the present invention as well as a human food product, food supplement, animal feed and/or fish feed composition comprising such a nutrient source.

Depending on which specific fungal strain is chosen, different results are to be expected. For instance, amongst the currently investigated strains *Neurospora intermedia* has the highest potential for ethanol production from thin stillage, with a production of approximately up to 5.5 g/L. *Aspergillus oryzae* on the other hand results in more fungal biomass, but with a corresponding lower ethanol production (approximately up to 1.7 g/L). The tested zygomycetes strain, *Rhizopus* sp., results in both lower ethanol and biomass production, but the biomass contains chitosan which is not found in the ascomycetes biomass.

A human food product, food supplement, animal feed and/or fish feed composition typically comprises a nutrient source according to the present invention in an amount of at least 5% (w/w), such as at least 7.5% (w/w), such as 10%, 20%, 30%, 40%, 50%, 60%, 70%, 80%, 90% or 99% of the total dry weight of the food product, food supplement, composition or feed as a substitute for, or a supplement to the standard protein source.

In one embodiment, a human food product, food supplement, animal feed and/or fish feed composition typically comprises a nutrient source according to the present invention in an amount of at the most 100% (w/w) of the total dry weight of the food product, food supplement, feed or composition as a substitute for, or a supplement to the standard protein source.

The hyphae of the filamentous fungi used in the integrated second generation process for producing bioethanol comprising at least one fungal cultivation stage of the present invention are non-septate and their cell walls consist mainly of chitosan. Thus, the invention further relates to a chitosan source for use in biomedical and environmental fields comprising a fungal biomass produced according to the present invention.

FIGURE LEGENDS

FIG. 1A: Ethanol production from grains (first generation process)

FIG. 1B: Ethanol production from lignocelluloses (second generation process)

FIG. 2A Integration at the fermentation stage, DDGS production comprising fungal biomass FIG. 2B Integration at the fermentation stage, production of DDGS and separate fungal biomass FIG. 2C Integration at the fungal cultivation stage, DDGS production comprising fungal biomass FIG. 2D Integration at the fungal cultivation stage, production of DDGS and separate fungal biomass FIG. 3: All of these strains have been confirmed to grow on mostly wheat-based thin stillage in aerobic conditions, resulting in the production of fungal biomass and ethanol.

FIG. 4: Even though the market values of both the raw material and the ethanol have a strong correlation with the price of fossil fuel, individual fluctuations still occur.

FIG. 5: The fungal biomass would then replace part of the animal feed, including fishmeal which has more than quadrupled in price from January 2000 to April 2013, ending with an average price of 1,849 USD/ton FIG. 6: Table 1: Final biomass and spent thin stillage characteristics after 72 h cultivation with Ascomycetes fungi. [a]ND—not determined; [b]TS—Total solids; [c]SS—Suspended solids FIG. 7: Table 2: Protein and lipid composition of industrial DDGS (dry distiller grains with solids) and *N. intermedia* biomass obtained from 48 h cultivation in bubble column reactor.

FIG. 8: Ethanol concentration (A) and ethanol productivity (B) during continuous cultivation of *Neurospora intermedia* in thin stillage.

FIG. 9: Table 3: Characteristics of the thin stillage used in batch and continuous culture of *Neurospora intermedia*. [a] Thin stillage used for batch cultivation
[b] Thin stillage used for continuous cultivation
[c] Not detected FIG. 10: Table 4: Protein and lipid composition of industrial DDGS (dry distiller grains with solids) and *N. intermedia* biomass obtained from a 48 h cultivation in bubble column reactor. *Distillers dried grains with solubles
**Not determined FIG. 11: Proposed inclusion of *Neurospora intermedia* in the overall industrial process of ethanol production for production of biomass and extra ethanol from thin stillage (boxes highlighted in grey).

FIG. 12: Ethanol (A) and biomass dry weight (B) profiles obtained during 48 h cultivation of *Neurospora intermedia* in airlift (straight lines) and bubble column (dashed line) at 0.5 (♦), 1 (■), 1.5 (▲), and 2 vvm (●). All conditions were tested in duplicate and all error bars represent two standard deviations.

FIG. 13: Ethanol concentration (A) and ethanol productivity (B) during continuous cultivation of *Neurospora intermedia* in thin stillage.

FIG. 14: Biomass dry weight (A) and biomass productivity (B) during continuous cultivation of *Neurospora intermedia* in thin stillage.

FIG. 15: Profiles of arabinose, glucose and xylose in thin stillage liquid fraction during batch (A) and continuous (B) cultivation of *N. intermedia* in the bubble column. Errors bars represent two standard deviations.

FIG. 16: Profiles of arabinan and galactan (A) and glucan, mannan and xylan (B) in thin stillage solid fraction during batch and continuous cultivation of *N. intermedia* in the bubble column. Errors bars represent two standard deviations. "BC" stands for the batch process in the bubble column and "Cont." stands for the continuous cultivation.

FIG. 17: Table 5: Analysis of content of fungal biomass washed.

FIG. 18: Profiles of ethanol and contamination-derived acids during cultivation of *Neurospora intermedia* in 20 m$^3$ thin stillage. The lines represent from the top to the bottom: succinic acid, lactic acid, ethanol and acetic acid.

FIG. 19: Dissolved carbohydrate oligomers of glucose (grey), xylose (green), arabinose (stripes), galactose (orange) and mannose (white) in the liquid fraction of whole stillage before fungal cultivation (untreated), after fungal cultivation without enzyme addition (no enzyme) and with addition of 1 FPU cellulase/g suspended solid (1 FPU).

FIG. 20: Ethanol production profiles during *N. intermedia* cultivation in whole stillage supernatant (circles), centrifuged particles (squares) and sieved large particles (triangles) with (dashed lines) and without (straight line) cellulase addition. Error bars represent two standard deviations.

FIG. 21: Total yield (g/g dry bran biomass) of arabinan, glucan, and xylan polysaccharides after the dilute phosphoric acid pretreatment and subsequent enzymatic hydrolysis (48 h); and ethanol released after the subsequent fermentation (48 h) with *N. intermedia*.

FIG. 22: Xylose concentration after pretreatment at 150° C. (♦), 170° C. (■), 190° C. (▲) and 210° C. (x) with 1.75% phosphoric acid at 5-20 minutes.

FIG. 23: Ethanol production during cultivation with *N. intermedia* on dilute phosphoric acid pretreated wheat straw. The lines represent straw with addition of all nutrients (■), without vitamins and trace metals (▲), without $(NH4)_2SO_4$ (●), without $KH_2PO_4$ (♦), without CaCl2 (+), without $MgSO_4$ (–) and without nutrients (x).

DETAILED DESCRIPTION OF THE INVENTION

Bioethanol Production

Almost any plant-based material can be an ethanol feedstock. All plants contain sugars, and these sugars can be fermented to make ethanol in a process called "biochemical conversion." Plant material also can be converted to ethanol using heat and chemicals in a process called "thermochemical conversion".

Some plants are easier to process into ethanol than others. Some don't require many resources to grow, while others need many resources, as well as intensive care. Some plants are used for food as well as fuel, while others are cultivated exclusively for ethanol. Even plant-based wastes can be made into ethanol. Climate and soil type determine the types and amounts of plants that can be grown in different geographic areas.

Starch- and Sugar-Based Ethanol Feed-Stocks

Nearly all ethanol is derived from starch- and sugar-based feed-stocks. The sugars in these feed-stocks are easy to extract and ferment, making large-scale ethanol production affordable. Corn is the leading U.S. crop and serves as the feed-stock for most domestic ethanol production. Small amounts of wheat, milo and sugarcane are used in the US, although the economics of these are not as favorable as corn.

Cellulosic Ethanol Feed-Stocks

Cellulosic feed-stocks are non-food based feed-stocks that include crop residues, wood residues, dedicated energy crops, and industrial and other wastes. These feed-stocks are composed of cellulose, hemicellulose, and lignin (typically extracted to provide process steam for production).

To determine the potential volume of ethanol produced (via biochemical conversion) per ton of various feed-stocks, the person skilled in the art uses the commonly available "Theoretical Ethanol Yield Calculator" (http://www.energy.gov/eere/bioenergy/bioenergy-technologies-office) and/or the "Biomass Feed-stock Composition and Property Database" (http://www.afdc.energy.gov/biomass/progs/search1.cgi). The Energy Research Centre of the Netherlands' "Phyllis database" (https://www.ecn.nl/phyllis2/) also contains information on the composition of biomass and waste.

First Generation Bioethanol

The first generation ethanol plants utilize either sugars or starch. The sugar-based ethanol plants are predominantly produced in Brazil from sugarcanes. The starch-based ethanol is generally from corn but also from grains, and is dominated by the U.S. followed by other major ethanol producing countries such as China, Canada, France, Germany, and Sweden. In the global market, ca. 21 million m$^3$ ethanol is produced from sugarcane, while ca. 60 million m$^3$ ethanol is produced from corn and grains (REN21, 2012). The starch-based process will be in focus here. There are more than 200 such plants in the U.S. with an average capacity of about 260,000 m³/year ethanol producing from corn or sorghum (www.ethanolproducer.com).

The first step of the ethanol production from grains (FIG. 1) in the process called dry mills is the milling of the substrate and subsequent liquefaction of the starch. The liquefaction is followed by the hydrolysis or saccharification, which releases the sugar (glucose) monomers into the solution. During the subsequent, or simultaneous fermentation with yeast (*Saccharomyces cerevisiae*), the sugar monomers are converted into ethanol and carbon dioxide. Usually an ethanol concentration of ca. 10% (w/v) is obtained at the end of the fermentation. The fermentation liquid, or beer, is distilled to separate and purify the ethanol, which is then dehydrated to concentrations above 99.7% for fuel applications, according to the European standard EN 15376. In the bottom of the distillation column, the stillage consisting of about 10% TS (total solids), including residual substrate, yeast, and fermentation by-products, is accumulated. Some of the solid particles are removed from the liquid via centrifugation by a decanter and the remaining thin stillage is sent to an evaporator. The centrifugation cake and resulting syrup from the evaporation are normally mixed to produce Distillers Dried Grains and Solubles (DDGS). The DDGS, which is principally a protein source as animal feed, plays a crucial role in the overall process economy.

Considering the vast amount of accumulated knowledge gathered from decades of industrial production of the first generation ethanol process, there are very few uncertainties involved in the process, raw materials, and the markets. Thus, even if the process only provides a low rate of return, it comes with relatively low risk, which is mainly based on uncertainties regarding the cost of the feed-stock and the price of the products: ethanol and animal feed (DDGS). However, the use of potential human food as feed-stock for the process has led to considerable ethical discussions, normally referred to as the "food vs. fuel" debate, with widely diverse and strongly polarized views. The supply of the feed-stock can also become a potential limiting factor compared with the potential demand. It is a complex issue that is discussed in its own forum. This debate also results in propositions for new laws and regulations to push the ethanol plants to direct their expansion away from food-based feed-stock, which causes some uncertainties regarding future plans.

Second Generation Bioethanol

Second generation ethanol utilizes different types of lignocellulosic materials as substrate. Currently, only negligible amounts of second generation bioethanol are produced in several demo plants around the world that work industrially, but are not yet commercially feasible. The ethanol is produced from the sugar monomers released as a by-product during their sulfite process. Historically, more ethanol however has been produced from lignocellulosic feed-stock. As an example, during the 1940s more than 30 sulfite mills were in operation in Sweden, all of which included ethanol production, and by the end of the 1980s Soviet sulfite mills had a production capacity of up to 190,000 m³/year. The second generation bioethanol process will most likely be partly similar to the first generation process.

Second generation ethanol processes have technically no issues with feed-stock supply, as 7-18 billion tons/year of lignocellulosic biomass is available for human exploitation. Instead, the process is currently limited by technical and by economic challenges (the cost of lignocellulosic feed-stock, including its transportation, often compete unfavorably with the efficient supply chain of sugar or starch containing raw materials), which although connected can be divided into three groups. The first technical challenge is caused by the recalcitrance of the biomass and thus the need for relatively harsh pretreatments of the feed-stock. This harsh pretreatment, in turn, results in the formation of inhibitory compounds, which causes problems during the fermentation. Numerous reviews can be found on the topic, e.g., by Taherzadeh and Karimi (2008). The second challenge is in the production of efficient enzymes to hydrolyze the cellulose, at a cost competitive to the first generation enzymes hydrolyzing starch. Although major improvements have been accomplished by the enzyme manufacturers, reducing the cost of the enzyme to 0.13 USD/L ethanol, improvements are still necessary. Thirdly, sufficiently high ethanol concentrations in the beer have to be reached in order to reduce the cost of distillation and wastewater treatment. A goal of 4-4.5% (w/v) is generally considered. This might appear to be a minor issue, but reaching it requires substrate loadings above 15% with subsequent mixing and inhibitor problems.

A number of lignocellulosic materials also release high amounts of pentose sugars during hydrolysis. Corn stover, wheat straw, and switch grass are examples of lignocellulosic materials with xylan contents above 20% on a dry weight basis; more than half of the glucan content in the corresponding materials. Since the microorganism of choice, *S. cerevisiae*, is unable to utilize pentoses, this can become an issue. A plethora of examples of genetic manipulation to overcome this issue exists in the literature. However, although the results are promising, improvements are still necessary. Furthermore, legal issues and consumer opinions regarding the use of genetically modified organisms, especially in Europe, are often overlooked.

Process Integration

A possible solution to use all the current dry mills for the second generation ethanol production and also decrease the high risk of investing in a new second generation ethanol process is to integrate lignocellulosic ethanol into the current dry mills. In principle, most of the dry mills have access to lignocelluloses produced together with the grains such as straw, corncob, bran, etc. with a relatively low transportation cost. An example of how this process integration could be carried out is depicted in FIG. 2 with two different proposed solutions: (a) integration at the fermentation stage and (b) integration at the fungal cultivation stage. In both cases, the first generation process remains mostly unchanged, although not completely unaffected. A larger potential influence on the first generation ethanol process is carried out by the alternative (a), as the inhibitors from the second generation process could enter the fermentor(s). Considering the dilution effect, it is rather unlikely that these inhibitors would disrupt the fermentation. New residuals, such as mainly lignin and undigested cellulose, will also pass through the entire process. Nevertheless, bringing an unknown factor into the heart of the process is not usually popular for plant managers, which could prevent implementation of the integrated process. If the integration is performed in the later steps, i.e., at the new suggested step "fungal cultivation" (see section 4), the heart of the first generation process would be untouched. This would also minimize the amount of sugar (pentose) rich process streams in use, and thus the risk of unwanted reactions and contamination.

One of the major challenges of the lignocellulosic ethanol processes is obtaining sufficiently high sugar concentrations after the hydrolysis. To a large degree, this is solved by integrating the first and second generation processes, since sufficiently high concentrations are easily reached in the first generation. Thus, lower concentrations of the lignocellulosic feed-stock are required, which considerably reduce the problems associated with mixing of the slurry. The lower concentrations will also lead to lower concentrations of inhibitors formed during the pretreatment, resolving the need for detoxification. Other than being less challenging, the pretreatment and hydrolysis will most likely be very similar to any second generation process. Thus, the pretreatment will most likely utilize acids or bases to open up the structure. However, care must be taken because the chemicals have to be chosen so that they do not negatively influence the quality of the animal feed product (DDGS). The hydrolysis will probably use enzymes and could either be carried out in a separate vessel or together with the fermentation, and would most likely not influence the quality of the DDGS. Following hydrolysis, the liberated hexoses will be converted into ethanol and $CO_2$ by the fermenting microorganism as usual.

A potential integration of the first and second generation ethanol processes, however, does not solve the problem of how to utilize the pentoses. A possible solution would be to use genetically modified strains of *S. cerevisiae*, however, especially for the European market legislations and negative public opinion is likely to become an issue. Other microorganisms capable of fermenting pentoses into ethanol could also be employed, but they are generally quite sensitive to inhibitors (including ethanol), which could become an issue, especially on the industrial scale. Co-fermentation of pentoses and hexoses are also yet to be solved. However, the pentoses could also be used for the production of compounds other than ethanol at later stages in the process.

The best opportunity for late utilization of pentoses is most likely after the separation of most of the solids from the stillage, i.e., the thin stillage (FIG. 2). However, a dedicated process step solely for pentose utilization in an integrated first/second generation process is not likely to be economically optimal due to the relatively low concentrations. Still, unfermented substrate (including carbohydrate polymers), dead yeast cells, and metabolites are likely to remain in relatively large quantities in the thin stillage as well. Therefore, a method to utilize both pentoses and the other residues is needed. Furthermore, since the animal feed product DDGS plays a crucial role in the process economy of existing first generation plants, its quality must not be compromised. This significantly reduces the number of potential solutions, as the microorganism essentially has to be food-grade.

Fungal Cultivation and Pentose Utilization

A proposed solution to the utilization of unfermented substrate without compromising the quality of the DDGS is to use food-related strains of Zygomycetes and Ascomycetes filamentous fungi. Potential strains include *Rhizopus* sp. isolated from tempe; *Fusarium venenatium* used for the production of Quorn; *Aspergillus oryzae* from e.g., sake fermentation; *Neurospora intermedia* isolated from oncom (fermented food based on left-overs in Indonesia); and *Monascus purpureus* used for the production of red rice. All of these strains have been confirmed to grow on mostly wheat-based thin stillage in aerobic conditions, resulting in the production of fungal biomass and ethanol (FIG. 3). The fungal biomass can then easily be separated from the liquid due to its filamentous nature and dried. The ethanol will remain in the fermented broth, which is sent to the evaporators. The volatile ethanol will naturally join the outgoing steam, which is condensed and sent back into the process. Thus, no additional process steps will be required to separate the ethanol.

For pentose utilization and second generation processes, the focus among these filamentous fungi has been on the Zygomycetes. The research was initiated by with the use of sulphite liquor from the paper pulp industry as a substrate for *Rhizopus*, and has been ongoing since then. The general trend has been that while the ethanol yield from xylose is most often limited (ca. 0.2 g/g), the production of fungal biomass has been more promising (ca. 0.35 g/g). These ethanol yields from xylose can also be considered close to what is achievable, since all the evidence suggests that Zygomycetes follow the general fungal pathway, resulting in an imbalance among the redox carriers. Without access to oxygen, it is not possible for the cells to correct this imbalance, which prevents anaerobic fermentation of xylose by these fungi. Thus, the need for aeration adds a natural limitation to produce ethanol, especially in industrial scale, which prevents the required micro-adjustments in the oxygen level for obtaining a high ethanol yield. The production of fungal biomass, which is the best in aerobic conditions, can probably still be optimized from pentoses by adjusting the process parameters and the feed composition. Considering that utilization of xylose for biomass production requires aerobic conditions, aeration has to be considered an important factor. This is also true for the Ascomycetes strains. Aeration is also a crucial factor to decompose carbohydrate polymers in the thin stillage; metabolites from the fermentation and infections such as glycerol, lactic acid, and acetic acid; low concentrations of unfermented sugars such as xylose; and yeast cells lysis products. All of these compounds either require oxygen to be utilized by the fungi or the utilization is considerably enhanced by oxygen. Many of the compounds also need to be degraded enzymatically in order to be accessible to the fungi. The fungi, however, are known to be able to produce e.g., amylases, cellulases, proteases, and lipases and can thus utilize most substrates (Ferreira et al., 2013a). Similar enzyme production by different Ascomycetes is also very well known, including enzymes for more uncommon reactions (Zelinski & Hauer, 2002). Since the production of enzymes increases the energy expenditure of the cells, good access to ATP generating processes is required. This further increases the importance of aeration.

Cultivation of filamentous fungi is not without challenges. Mixing can particularly become an issue due to the broth viscosity caused by the filamentous nature of the cells (Gibbs et al., 2000). The fungi may also attach to the equipment inside the reactor such as baffles and impellers. There are two possible ways to counteract this phenomenon. One is to adjust the process conditions and try to control the growth morphology. For instance, pellets (small beads consisting of intertwined hyphae) can be formed if the conditions are controlled (Nyman et al., 2013) to reduce the broth viscosity. However, growth in the form of pellets instead of free mycelia/clumps has been shown to both increase and decrease the metabolite yields, depending on the strain and the metabolite. Thus, growth in the form of pellets is not always beneficial. The other way to solve the problem is to adjust the cultivation vessel to fit the growth of the filamentous fungi. For instance, air-lift and bubble-column type reactors have been performing well for fungal cultivations on the thin stillage in aerobic conditions (unpublished data). The common factor between these two types of reactors is that they lack internal moving parts, and the mixing is achieved via the aeration process. This also has the benefit of a relatively low energy demand for the mixing.

Benefits of Biomass Production

Although the first generation ethanol production is a well-known process with few uncertainties, it is still very dependent on the raw material cost and the selling price of ethanol and DDGS. Even though the market values of both the raw material and the ethanol have a strong correlation with the price of fossil fuel, individual fluctuations still occur (FIG. 4). Since the profit margins are relatively small, these fluctuations represent a considerable risk to the process economy.

One way to decrease the impact of substrate/production price fluctuations is to follow the biorefinery concept and produce more than one product. Edible Zygomycetes or Ascomycetes fungal biomass have the potential to fulfill this role as an additional product. The fungal biomass could either be used to improve the quality of the DDGS, or be sold separately. The first alternative has the advantage of being relatively easy to implement. The second alternative has the potential advantage of providing the highest price. This can mainly be attributed to the high protein content (>50%), which makes it potentially useful as a high-value animal feed, including use as a fish feed component. The fungal biomass would then replace part of the fishmeal, which has more than quadrupled in price from January 2000 to April 2013, ending with an average price of 1,849 USD/ton (FIG. 5). The demand is also likely to remain high, as more and more fish are produced in aquacultures.

Fungal biomass could also find other uses. Some strains are known to produce valuable lipids, which could be extracted from the biomass and sold as e.g., dietary supplements. Low-grade fatty acids could instead be used for e.g., biodiesel production. If the fungi are cultivated, the cell wall fraction of the biomass could be used as a source of chitosan, or be used to produce a bio-based superabsorbent. However, all these applications require additional process steps after the harvesting and their economic benefit is unknown.

Cultivation of filamentous fungi provides benefits other than an additional product; there are also process related advantages such as easy separation of the produced mycelium. A major potential advantage can be found in the evaporators, which have the challenging task of removing as much water from the thin stillage as possible. Fouling, in particular, and the viscosity of the liquid can be major obstacles in the process. By reducing the total amount of suspended solids and organic compounds in the liquid, the severity of these obstacles could be decreased. This could allow more water to be removed in the evaporators and less in the driers. It could also allow more of the thin stillage to be sent back into the process as back-set, which would directly decrease the load on the evaporators and the driers.

Conclusion

Integration of second and already existing first generation ethanol processes is an attractive way to reduce the investment costs and risks compared to a standalone second generation processes. However, since most of today's ethanol production is based on starch and thus dependent on by-products sold as e.g., animal feed to be economically feasible, the integration cannot adversely affect these by-products. This severely limits the possible ways to utilize the pentose sugars released from the lignocellulosic feed-stock. The proposed solution is to use edible Ascomycetes filamentous fungi, which are naturally capable of utilizing pentoses, but also other unfermented substrates left after distillation.

EXPERIMENTS

Experiment 1

Ethanol and Biomass from Thin Stillage in Lab and Pilot Bioreactor

Thin stillage is a by-product from dry-mill starch-based ethanol production. Simplified after distillation there are two streams, the top stream with a high ethanol concentration and the bottom stream, containing the residues usually referred to as whole stillage. After removal of the larger solids through centrifugation the remaining liquid is referred to as thin stillage.

In this experiment, four different Ascomycetes fungal strains have been cultivated on thin stillage: *Aspergillus oryzae*, *Fusarium venenatum*, *Monascus purpureus* and *Neurospora intermedia*. The strains were compared and evaluated with a focus on ethanol production in shake flasks. All of these fungi were able to grow and also produce ethanol.

Maxima of 1.9, 1.6, 0.4 and 4.8 g/L of ethanol was achieved from *A. oryzae*, *F. venenatum*, *M. purpureus* and *N. intermedia*, respectively. Thus, *N. intermedia* was the most promising strain. Cultivation of these fungi also resulted in reduction of the total solids and suspended solids of the thin stillage, which for *N. intermedia* reached 34 and 69% reduction, respectively. A summary of the results can be seen in table 1 (FIG. 6).

The growth of *N. intermedia* on the stillage was also evaluated in a small pilot of 26 L airlift- and bubble-column bioreactor in batch processes. Maximum ethanol production of 3.2 and 3.5 g/L was reached from the two types of reactors, respectively. Simultaneously 5.3 and 5.0 g/L of fungal biomass was produced, containing ca 50% crude protein (see table 2 (FIG. 7) for further information). The fungus was also cultivated using a continuous process in the bubble column, which resulted in the production of 5.1, 3.8 and 3.1 g/L ethanol at production rates of 0.57, 0.68, and 0.78 g/L/h at dilution rates of 0.10, 0.15, and 0.20 $h^{-1}$, respectively (FIG. 8).

Experiment 2

Abstract

Ethanol processes in dry mills produce ethanol and animal feed from whole grains, where the wastewater after the distillation and separation of solid materials is called "thin stillage". In this work, similar production of ethanol (3.5 g/L) and biomass (5 g/L) from thin stillage was obtained during batch cultivation of the edible fungus *Neurospora intermedia* in a 2 m high airlift reactor and bubble column. The fungal biomass, containing 50% (w/w) protein and 12% (w/w) lipids, was rich in essential amino acids and omega-3 and -6 fatty acids. In continuous mode of fermentation, dilution rates of up to 0.2 $h^{-1}$ could be applied without cell wash-out in the bubble column at 0.5 vvm. At 0.1 $h^{-1}$, around 5 g/L of ethanol and 4 g/L biomass containing ca 50% protein were produced. The fungus was able to assimilate oligomers in the liquid fraction as well as sugars backbones such as xylan and arabinan in the solid fraction. The inclusion of the current process can lead to the production of 11,000 $m^3$ of ethanol (5.5% improvement), around 6,000 tons of high-quality biomass for animal feed, and energy savings considering a typical facility producing 200,000 $m^3$ ethanol/year.

1. Introduction

The process of ethanol production from sugar- and starch-based materials is well developed at industrial scale. Brazil and USA dominate the worldwide production of ethanol using mostly sugarcane and corn as feed-stocks, respectively. Beyond ethanol, animal feed nutrients commonly known as distillers dried grains with solubles (DDGS) are also produced during the process when grains (e.g. corn and wheat) are the substrates. The ethanol sector has produced ca 86 million tons of ethanol and 68 million tons of DDGS in 2011. However, fluctuations on the price of the feed-stock and produced products together with the energy-intensive character of the process might impose constraints to its overtime feasibility. Accordingly, research towards process improvement and diversification has been carried out mostly via valorisation of thin stillage. Thin stillage corresponds to the liquid fraction after whole stillage centrifugation (distillation left-overs), 15% of which is normally recycled as back-set water, while the remaining goes through a series of evaporations. The resulting condensate is also sent back to the process, whereas the concentrated syrup is normally dried together with the centrifuged solids to give rise to the DDGS (Taherzadeh et al 2013). Therefore, the processing steps leading to the production of DDGS are responsible for a large fraction of the overall process energy. The production of a variety of products including ethanol, cell-oil, feed nutrients, biogas, and eicosapentaenoic acid (EPA) have been investigated using thin stillage as cultivation medium. In addition to the production of new products, the employed microorganisms reduce the solid content of the thin stillage. Therefore, the viscosity of the medium is lowered which facilitates the series of evaporations and the following drying process. More thin stillage could also be used as back-set (lowering the load on the evaporators and driers) and the overall process energy consumption would be reduced.

Filamentous fungi have been giving an important contribute to the global economy via production of a plethora of important products including antibiotics, enzymes, organic acids, human/animal food products among many others (Gibbs et al 2000). Particularly, in a context of production of biomass for feed applications, filamentous fungi possess an important advantage over e.g. yeasts since they can be easily separated from the fermentation broth without requiring a centrifugation step. The ascomycete *Neurospora intermedia* has been previously successfully used for production of protein-rich biomass and ethanol from mostly wheat-based thin stillage which can potentially assume a very important role on the improvement of the process economics. This fungus is traditionally used for preparation of oncom, an indigenous Indonesian food, so that it can be classified as GRAS which is a great advantage if the fungal biomass is produced for animal or human consumption. With its inclusion in the established industrial process, the biomass would join DDGS as animal feed nutrients, while the extra ethanol produced could be send back to the process with the condensate as it is already done at industrial scale (Lennartsson et al 2014). However, the cultivation of filamentous fungi in bioreactors can be troublesome due to their filamentous growth. If stirred-tank reactors are used, the fungal filaments have the tendency to entangle with the inner parts such as baffles and impellers leading to sub-optimal mass and energy transfer rates. Airlift reactors and bubble columns have been alternatively developed and better process performances have been reported. Their main difference is the absence of inner parts e.g. baffles and impellers being the medium mixed by the supplied air. The aeration rate greatly influences fungal growth, metabolite production and assimilation of medium nutrients. For instance, higher aeration gives rise to higher biomass and lower ethanol productions, while assimilation of xylose is not possible under anaerobic conditions.

In this work, a thorough study was carried out on the influence of using different reactor designs and cultivation modes on the production of *N. intermedia* biomass and its composition, ethanol and characteristics of the derived thin stillage. At a first stage, the research focus was on the effect of the aeration rate using a 2 m high airlift reactor in batch mode; selected conditions were further compared with the reactor operating as a bubble column. At a second stage, continuous cultivation of *N. intermedia* in thin stillage was investigated in the bubble column reactor. To the best of our knowledge, this work reports for the first time a continuous process in bubble column using thin stillage as cultivation medium and *Neurospora intermedia* as catalyst.

2. Materials and Methods

2.1. Microorganism

The ascomycete *Neurospora intermedia* CBS 131.92 (Centraalbureau voor Schimmelcultures, The Netherlands) was used throughout this study. The strain was maintained on potato dextrose agar (PDA) slants containing (in g/L): glucose 20, agar 15, and potato extract 4. The slants were renewed every six months. New PDA plates were prepared via two days incubation at 30° C. followed by storage at 4° C. The spore solution was prepared by flooding the plates with 10 mL sterile distilled water; a disposable plastic spreader was used to extract the spores. Spore number was determined by using a counting chamber.

2.2. Thin Stillage

Thin stillage used in this work was provided by Lantmännen Agroetanol (Norrköping, Sweden), an ethanol production facility mostly based on wheat grains. The two spaced in time 1 m³ thin stillage batches were stored in 230 L barrels at 4° C. prior to use. Before cultivation, the thin stillage was sterilized at 121° C. for 30 min in an autoclave (Systec, Germany).

2.3. Cultivation in bioreactor

Cultivations at different aeration rates namely 0.5, 1.0, 1.5, and 2 vvm (air volume per culture volume per minute) were randomly carried out in a 2 m high, 15 cm diameter airlift reactor with 26 L total volume of the internal-loop tube reactor model (Bioengineering, Switzerland). The reactor was sterilised in situ with injection of steam (121° C., 30 min). Twenty liters of thin stillage were supplemented with 50 µL/L antifoam (Antifoam silicone snapsil FD 10, VWR International, USA) and adjusted to pH 5.5 with 10 M NaOH. A 24 h inoculum containing 8.8±0.9 g/L biomass dry weight (average value determined from measurements in triplicate) was prepared in three 1 L Erlenmeyer flasks containing 0.1 L thin stillage adjusted to pH 5.5 with 10 M NaOH. The inoculum was prepared via incubation in a water bath set at 35° C. and shaking at 125 rpm. The spore concentration was 8.7 (±1.6)×10⁸ spores/L. The cultivation temperature in airlift was maintained at 35±0.4° C. Cultivation was followed by taking 0.25 L samples every 12 h for a period of 48 h. The thin stillage was poured through a sieve, to recover the biomass, and stored at −20° C.; the harvested biomass was extensively washed with distilled water until a clear effluent was obtained. For comparative purposes, the reactor was transformed in a bubble column by removing the internal loop tube. The cultivation was carried out as above at the aeration rate of 0.5 vvm.

Continuous cultivation was also carried out in the bubble column reactor at 0.5 vvm. Three dilution rates namely 0.1, 0.15 and 0.2 h$^{-1}$ were sequentially applied after one day batch cultivation. The feeding medium, adjusted to pH 5.0-5.5 with 10 M NaOH, was supplied using the reactor-coupled peristaltic pump. Cultivation conditions, thin stillage storage, and biomass harvesting were done as above except that samples of 1 L volume were taken. Four 20 L volumes were replaced at each dilution rate. All batch and continuous cultivations were done in duplicate.

2.4. Cultivation in Shake-Flasks

*Neurospora intermedia* was cultivated in semi-synthetic medium containing either acetic acid (5 g/L) (Sharlau Chemie), L(+)-arabinose (Sigma Aldrich), D(+)-galactose (Acrös Organics), D (−)-glucose (Fisher Chemical), glycerol (Sharlau Chemie), DL-lactic acid (Acrös Organics), D(+)-mannose (Fluka) or D(+)-xylose (10 g/L) (Sigma Aldrich). The ascomycete was also cultivated in a mixture of these carbon sources containing (in g/L): acetic acid 1.0, lactic acid and glycerol 10, and the remaining carbon sources 2. The medium was supplemented with yeast extract (ratio carbon source/yeast extract of 4), salts and trace metals according to (Millati et al 2005) Millati, et al. The pH of sugar-containing and acid-containing media was adjusted to 5.5 with 1 M or 10 M NaOH, respectively, prior sterilization for 20 min in an autoclave (Systec, Germany). Cultivations were carried out in 250 mL Erlenmeyer flasks containing 50 mL of medium shaking at 125 rpm using a water bath set at 35° C. for 42 h. The spore concentration was 2.3×10$^8$ spores/L. At the end of cultivation the biomass was harvested using a sieve, except for that grown in acetic acid, arabinose and lactic acid-containing medium which was recovered by vacuum filtration, and washed extensively with distilled water. All cultivations were performed in duplicate.

2.5. Analytical Methods

The harvested biomass, reported as biomass dry weight in g/L, was dried until constant weight in an oven for 24 h at 70° C. The protein content of the biomass and thin stillage reported as crude protein and Kjeldahl nitrogen, respectively, was determined according to the Kjeldahl method using block digestion and steam distillation. The equipment included an InKjel P digestor and a Behrotest® S1 distiller (Behr Labor-Technik, Germany). Digestion was carried out by adding 20 mL of 98% $H_2SO_4$, antifoam and KT1 tablets (Thompson & Capper ltd, United Kingdom) to 0.4±0.0 g material for a total duration of 100 minutes at 100% power (of which 10 min for heating up the system). Digestion was followed by neutralization of the digested solution with 32% NaOH and distillation for 5 min. The distillation vapor was trapped in 50 mL of 4% $H_3BO_4$. Final titration was carried out with 0.1 M of HCl until pH 4.6. A factor of 6.25 was used to calculate the crude protein content. Determination of amino acid composition of the biomass and thin stillage (SS-EN ISO 13903:2005) and fatty acid composition of the biomass (Karlshamn's analysis methods Nr 2.5.1 and Nr 2.5.2) was performed by Eurofins (Lidköping, Sweden). The biomass cell wall fraction reported as AIM (alkali-insoluble material) was determined according to Zamani and Taherzadeh (2010).

The total solids, suspended solids and their structural composition were determined according to the National Renewable Energy Laboratory (NREL) methods including "preparation of samples for compositional analysis" (NREL 2008a), "determination of structural carbohydrates and lignin in biomass" (NREL 2011), "determination of total solids in biomass and total dissolved solids in liquid process samples" (NREL 2008b), and "determination of sugars, by-products, and degradation products in liquid fraction process samples" (NREL 2008c).

The liquid fractions from thin stillage and NREL protocol-resulting samples were analysed using high-performance liquid chromatography (Waters 2695, USA). A hydrogen-ion based ion-exchange column (Aminex HPX-87H, Bio-Rad, USA) at 60° C. and 0.6 mL/min 5 mM $H_2SO_4$ as eluent for analyses of acetic acid, ethanol, glycerol, and lactic acid and a lead (II)-based column (Aminex HPX-87P, Bio-Rad) at 85° C. and 0.6 mL/min ultrapure water for separation of arabinose, galactose, glucose, mannose, and xylose were used together with a refractive index (RI) detector (Waters 2414). All samples for HPLC analysis were centrifuged for 10 min at 10000×g, and the supernatant was stored frozen at −20° C.

3. Results and Discussion

The treatment and use of thin stillage is primordial in order to achieve cost-effective and environmentally friendly ethanol production facilities. In dry mill processes, typically 6-7 L of thin stillage are produced per liter of ethanol (Wall et al 1983). Therefore, thin stillage is available in large quantities and can be used for production of other value-added products considering its relevant amount of nitrogen and carbon sources. Further in the process, energy savings during evaporation and drying can be achieved due to the lower content of solids of the resulting thin stillage. *N. intermedia* has previously shown high potential for production of ethanol and biomass from thin stillage without extra addition of nutrients. Therefore, the process having the fungus as central catalyst can have positive effects on the overall process economy via production of high-value products and energy savings due to the reduction of thin stillage solids. The proposed inclusion of the ascomycete in the established industrial process is depicted in FIG. 11. Filamentous fungi are traditionally non-fastidious microorganisms whereby they can generally been grown in media containing simply some carbon and nitrogen sources. The two commercial one m$^3$ batches used during this study were collected at different timeline in the process and composed of around 60% (w/w total solids) of potential carbon sources (including glycerol, lactic and acetic acids, ethanol and sugars from liquid and solid fraction of thin stillage) and of around 6% (w/w total solids) of nitrogen. The main differences between the different thin stillage batches were found to be the contents of lactic acid, glucose and arabinose in the liquid fraction and glucan and mannan in the solid fraction (table 3). In this work, the aeration effect on ethanol and biomass production by *N. intermedia* was studied in a 26 L capacity airlift bioreactor. The airlift was further used as a bubble column both under batch and continuous cultivation to investigate the possibility of using a cheaper and smaller reactor for production of biomass, ethanol and consequent reduction of thin stillage solids.

3.1. Ethanol

The effect of aeration rate on production of ethanol from thin stillage was first studied in a 26 L capacity airlift reactor in batch mode. When varying the aeration rate between 0.5 and 2 vvm, the maximum production of extra ethanol was 3.2±0.1 and 1.2±0.3 g/L, respectively (FIG. 12A). Maximum ethanol production rates were 88±43, 92±1, 70±1 and 50±13 mg/L/h after 24 h of cultivation at 0.5, 1.0, 1.5 and 2.0 vvm, respectively. For comparative purposes, the airlift reactor was used as a bubble column by removing the internal loop and the cultivation was performed at 0.5 vvm. As shown in FIG. 12A (dashed line) the ethanol production profiles between airlift and bubble column were similar. Maximum extra ethanol production and production rate were 3.5±0.2 g/L after 36 h and 131±20 mg/L/h after 24 h of cultivation, respectively. Therefore, production of ethanol from thin stillage by *Neurospora intermedia* can be carried out by using a simpler reactor.

Ethanol production was also studied in continuous mode using the 26 L bubble column at 0.5 vvm (FIG. 13A). Dilution rates of up to 0.2 h$^{-1}$ could be applied without cell wash-out (FIG. 14A). During the stable stage, before changing to the next dilution rate, the extra produced ethanol achieved were 5.1±1.0, 3.8±0.0 and 3.1±0.3 g/L and production rates were 568±63, 681±1 and 778±59 mg/L/h at dilution rates 0.1, 0.15 and 0.2 h$^{-1}$, respectively (FIG. 13B). The implication of using a continuous process for production of ethanol from thin stillage is that a reactor of 2,000 m$^3$, around 4 times smaller than that needed for a batch process of 36 h, would be sufficient considering a flow of 200 m$^3$ per hour. Furthermore, developing a cell-retention system for the current process would potentially have positive effects on achieving higher dilution rates and so much smaller reactors and less investment would be needed.

The distillation of the extra ethanol produced by *N. intermedia* from thin stillage would not need further investment. The alcohol would follow the normal stream of condensate after the series of evaporations as it is done nowadays at industrial scale. Based on the data obtained in this study, around 11,000 m$^3$ of ethanol can be produced by *N. intermedia* from thin stillage under continuous cultivation at dilution rate of 0.1 h$^{-1}$. Thus, the inclusion of *N. intermedia* would represent an improvement of 5.5% on the ethanol production considering a facility producing 200,000 m$^3$ ethanol/year.

3.2. Biomass Production and Characteristics

The production of biomass from thin stillage as a second value-added product was also investigated in this work. Similarly to ethanol production, the aeration rate applied in the airlift reactor influenced the production of biomass. By varying the aeration rate between 0.5 and 2 vvm, maximum produced biomass of 5.3±1.1 and 9.2±0.9 g/L were achieved, respectively (FIG. 12B). This biomass value is lower than that achieved in a previous work with shake-flasks experiments (Ferreira et al 2014)]. The observed differences can be related to differences in the thin stillage composition used or inefficient wash stage of the biomass since *Neurospora intermedia* grew as massive mycelial suspensions in shake flasks (Ferreira et al 2014). In the airlift, the ascomycete grew as small clumps of decreasing size for progressively higher aeration rates. Ferreira et al (2012 have observed the effect of better oxygen transfer rates when cultivating a filamentous fungus in spent sulphite liquor. They achieved clear improvement in biomass production when changing from shake-flasks to the airlift reactor. The crude protein of the dry biomass slightly decreased during cultivation in thin stillage at all tested aeration rates applied; crude protein ranges were 53.0±0.0-48.1±1.1, 51.7±1.9-49.2±1.6, 52.6±0.6-49.0±1.4 and 50.0±4.5-49.2±6.9% (w/w) at 0.5, 1.0, 1.5 and 2 vvm, respectively.

Similarly to production of ethanol, the maximum amount of biomass produced (5.0±0.3 g/L after 36 h of cultivation) achieved in bubble column was comparable to that in the airlift reactor (FIG. 12B—dashed line). Beyond continuous-stirred tank reactors, airlift reactors have also been developed as an alternative to bubble columns reactors. The internal loop of the airlift promotes a different mixing pattern that has been shown to lead to comparatively better mass and oxygen transfer rates. However, using a bubble column did not lead to differences in both ethanol and biomass production in this study. Perhaps, such effect would be seen if the process had been compared at higher aeration rates, using other reactor size and/or experimental set-up. Considering that the bubble column implies similar results and less investment costs if installed industrially, characterization at large extent of the biomass harvested after 48 h of cultivation was carried out. The crude protein fraction of *Neurospora intermedia* dry biomass was found to be of 52.9±6.5% (w/w); the amino acid profile was determined and accounted to 41.7±10% (w/w) of the biomass dry weight. As shown in table 4 (FIG. 10), all 9 essential amino acids to humans including phenylalanine, valine, threonine, tryptophan, methionine, leucine, isoleucine, lysine, and histidine were present in *Neurospora intermedia* biomass and accounted to around 40% of its composition. Comparatively to DDGS, a well-studied product from the ethanol industry traditionally used for animal feed, lysine content was double in *N. intermedia* biomass (table 4). The lipid content of the biomass (around 12% (w/w)) was mainly composed of linoleic acid (47.6±0.7%), palmitic acid (20.5±1.5%), oleic acid (15.3±0.4%), α-linoleic acid (4.6±0.1%) and stearic acid (3.8±0.2%). Therefore, the ascomycete lipid fraction was at large extent composed of polyunsaturated fatty acids (52.3±0.8%) of which 47.8±0.7% (w/w) were omega-6 fatty acids and 4.6±0.1% (w/w) were omega-3 fatty acids. These polyunsaturated fatty acids are considered as essential to human diet. The cell wall fraction of *N. intermedia* showed roughly a 60% increase during cultivation; it composed 18.9±0.4% (w/w) and 30.3±1.6% (w/w) of the biomass after 12 and 48 h of cultivation, respectively. A maximum of 1.5±0.1 g/L of AIM was obtained at the end of the cultivation. The cell wall of Ascomycetes has chitin has main component and although the presence of native chitosan has not been reported for these fungi, the extraction of chitosan has previously been carried out (Bartnicki-Garcia 1968; Hu et al 2004). The ash content of the biomass was 5.1±0.1% (w/w) at the end of cultivation.

In view of its protein, amino acid, lipid and fatty acid composition as well as its comparable profile of amino acids with that of DDGS, *N. intermedia* biomass is a potential source of high-quality nutrients for feed application. The extra biomass produced via inclusion of the present process would increase and diversify the amount of animal feed nutrients of the ethanol industry.

During continuous cultivation of *N. intermedia* in thin stillage, growth of lactic acid bacteria was detected after 72 and 36 h of cultivation for the replicates 1 and 2, respectively. However, the bacterial growth did not affect the production of ethanol: as can be seen from FIG. 14A there is a difference regarding biomass production between replicates between 24 and 66 hours of cultivation which was not observed for the ethanol production (FIG. 13A). Moreover, lactic acid bacteria did not take over of the cultivation, which is very relevant considering that industrial processes have bacterial contamination as main production constraint. The lactic acid concentration in the medium, which increased from 3 to 5 g/L with bacterial contamination, remained constant at all dilution rates applied.

Similarly to the ethanol concentration, the biomass production under continuous mode decreased for gradually higher dilution rates (3.6±0.9, 2.4±0.4 and 1.6±0.0 g/L at 0.1, 0.15 and 0.2 h$^{-1}$, respectively), while biomass production rates were similar at 0.1 and 0.15 h$^{-1}$ (363±93 and 366±61 mg/L/h, respectively) and decreased when the highest dilution rate was applied (315±4 mg/L/h) (FIG. 14B). The crude protein of the biomass after 66 h of cultivation (end of the first dilution rate) was analyzed and found to be 50.1±3.8% (g/g) on a dry basis.

Therefore, in view of the results obtained in this work, the inclusion of N. intermedia in the industrial process can lead to the production of high-quality biomass if the high content of protein and lipid and profiles of amino acids and fatty acids are considered. If a continuous process is installed at dilution rate of 0.1 $h^{-1}$, 6300 tons of biomass could be produced each year.

3.3. Thin Stillage

In addition to the production of ethanol and fungal biomass, the inclusion of N. intermedia in the industrial ethanol process can have a positive impact on thin stillage evaporation and drying steps via assimilation of organic matter. Cultivation of the ascomycete in the airlift reactor under different aeration rates led to reduction of 12-17% (w/v) (10-15 g/L) regarding total solids. The acetic acid present in the thin stillage was consumed after 12 h of cultivation, while glycerol and lactic acid concentrations were constant during cultivation at all tested aeration rates. Similar trends were found when cultivating N. intermedia in bubble column at 0.5 vvm regarding reduction of total solids (15.6±3.4% (w/v)), depletion time of acetic acid and maintenance of glycerol and lactic acid concentrations throughout cultivation. Clearly, N. intermedia preferred carbon sources other than glycerol or lactic acid. In semi-synthetic medium, the ascomycete had consumed all glycerol after 42 h of cultivation when it was the single carbon source in the medium. However, when the fungus was cultivated in a mixture of carbon sources, glycerol started to be consumed just when all hexoses and pentose sugars were depleted. N. intermedia hardly consumed lactic acid though; only 1 g/L of lactic acid had been consumed after 42 h of cultivation. The analysis of the dissolved oligormers and sugar polymers in the solid fraction was carried out and the findings are depicted in FIGS. 15 and 16. During batch cultivation, the concentration of arabinose, glucose and xylose decreased by 73.3±1.4, 73.3±2.5 and 79.5±0.9%, respectively. Galactose and mannose, present in lower amounts in thin stillage (table 3), were reduced by 42.5±0.7 and 11.6±1.9%, respectively. The total amount of carbon sources reduced in the liquid fraction was 16.0±0.1 g/L. Clearly, N. intermedia had the capability to assimilate the dissolved oligomers present in the thin stillage. This conclusion is supported by the comparatively much lower amounts of the monomeric sugars in the liquid fraction (table 3; FIG. 15 A). The enzymatic capability of N. intermedia was further unveiled after analysing the solid fraction of the thin stillage (FIGS. 16 A and B): arabinan, glucan, mannan, xylan and galactan had been reduced by 81.1±10.1, 56.7±3.2, 74.7±11.4, 91.3±1.7 and 69.6±2.7%, respectively. The total amount of carbon backbones reduced was 2.5±0.2 g/L. The release of monomers either from dissolved oligomers or from the sugar polymers in solid fraction is further supported by the increase in monomers arabinose (0.7±0.0 to 1.7±0.2 g/L) and xylose (0.6±0.0 to 1.6±0.3 g/L) concentrations. These increases are in complete agreement with a previous research work (Ferreira et al 2014). At the end of cultivation, the thin stillage pH was 6.2±0.1 and its ash content has been reduced by 31.9±13.1% (w/v).

During continuous cultivation, the concentration of glucose and xylose-based oligomers at the stable phase increased at gradually higher dilution rates (FIG. 15 A). Reduction of glucose was 64.4±3.5, 49.9±5.6 and 41.5±2.0, while reduction of xylose was 42.4±7.7, 20.3±6.1 and 6.2±4.3% at 0.1, 0.15 and 0.2 $h^{-1}$, respectively. The reduction of glucose and xylose in the liquid fraction was 14.7±1.6, 9.9±2.4 and 7.3±0.7 g/L at 0.1, 0.15 and 0.2 $h^{-1}$, respectively; reduction of arabinose, galactose and mannose was <0.5 g/L. Reasonably, the difference in the ethanol production after 24 h batch mode and that produced during the 24 h before starting the continuous cultivation is explained by the higher amount of glucose oligomers available to N. intermedia in the latter (table 3; FIGS. 12A and 13A). The reduction of xylan in the suspended solids decreased at gradually higher dilutions rates; reduction of 74.0±1.7, 70.2±1.8 and 63.6±8.9% (w/v) were obtained at 0.1, 0.15 and 0.2 $h^{-1}$, respectively. Such clear trend was not clearly observed for other sugar backbones present in the suspended solid; reduction ranges of arabinan, glucan, mannan and galactan were 61-67, 43-50, 22-42 and 48-54% (w/v), respectively. Total reduction amounts were 2.4±0.2, 2.8±0.9 and 2.5±0.7 g/L at 0.1, 0.15 and 0.2 $h^{-1}$, respectively. During continuous cultivation at dilution rate 0.1 $h^{-1}$, the reduction of measured sugars both in liquid and solid fraction (18.1±1.4 g/L) was comparable to that of total solids (16.9±3.8 g/L). Thus, at this dilution rate, the yield of ethanol was 303±9.5 mg/g of reduced solids. To the best of our knowledge, the only one work on production of ethanol from thin stillage is the one done by Gonzales et al (2010) Gonzalez, et al. The authors have reported an ethanol yield of 0.42 g/g based on consumed glycerol, maltose and glucose by Escherichia coli.

Continuous cultivation of N. intermedia at dilution rate of 0.1 $h^{-1}$ led to the reduction of 18% (w/v) of thin stillage solids including dissolved oligomers and sugar polymers in the solid fraction. Beyond being converted to mainly ethanol, $CO_2$ and biomass, the reduction of solids can have a positive impact on the energy savings of the overall production process. Removing water during the series of evaporations would be easier and so the amount of water to be removed in the driers would be lower. Furthermore, more thin stillage could be sent back to the process lowering the load on the evaporators and driers 4. Conclusions Production of ethanol and biomass by N. intermedia was successfully carried out both under batch and continuous cultivation using a 2 m high bubble column reactor. At the aeration rate of 0.5 vvm, up to 3.5 g/L of additional ethanol and 5 g/L of biomass could be produced in batch mode. The biomass, composed of around 50% (w/w) protein and 12% (w/w) lipids, was rich in essential amino acids and omega-3 and omega-6 fatty acids. During continuous cultivation dilution rates of up to 0.2 $h^{-1}$ could be applied without cell wash-out. At dilution rate of 0.1 $h^{-1}$, around 5 g/L of ethanol and 4 g/L of biomass were produced. Thin stillage solids have been reduced by 18% (w/v) including dissolved oligomers and sugar backbones (e.g. xylan and arabinan) from solid fraction. Considering an industrial facility producing 200,000 $m^3$ ethanol/year, the inclusion of the continuous production of ethanol and biomass from thin stillage by N. intermedia can produce 11,000 $m^3$ of ethanol, corresponding to a 5.5% improvement, and around 6,000 tons of high-value biomass for animal feed. Furthermore, the reduction of solids can have positive impacts on energy savings of the overall production process.

Experiment 3

20 $m^3$ Batch in a 80 $m^3$ Reactor
Method and Material:
Cultivation Conditions:
The temperature was kept at 35° C. during cultivation;
The working volume was 20 $m^3$ of thin stillage in a 80 $m^3$ reactor;

The initial pH of thin stillage was 4.0 and it was adjusted to 5.0 with 5.5 L 25% $NH_3$ and around 60 L of 45% NaOH.

Addition of antibacterial solution: 0 hours (5 L), 18 hours (5 L) and 37 h (20 L);

The aeration rate was 0.25 $m^3/m^3/min$;

No stirring was used;

An inoculum of around 70 L containing ca 40 g/L of fungal biomass was used; the inoculum was prepared in 50% thin stillage supplemented with glucose (100 g/L) and yeast extract (2 g/L) in fed-batch mode in a 26 L bubble column reactor at University of Borås;

Result:

The content of the fungal biomass produced was analyzed for protein, fat and two selective essential amino acids. See table 6 for results:

TABLE 6

|  | Fungal biomass | Non purified fungal biomass |
|---|---|---|
| Protein, (% of DS) | 56.20% | 51.6% |
| Fat, (% of DS) | 15.40% | 10.0% |
| Lysine (% of prot) | 5.71% | 3.5% |
| Methionine (% of prot) | 1.82% | 1.7% |

Discussion:

A lag phase of around 18 hours was observed;

The intended concentration of extra ethanol (0.4%) was almost reached within 24 hours of cultivation (the maximum ethanol production will be approximately between 24 and 36 hours of cultivation);

Therefore, the process of production of ethanol and biomass by N. intermedia from thin stillage has been successfully carried out in 0.02 $m^3$, around 1 $m^3$ and now at 20 $m^3$ working volumes.

Generally around 5 g/L of biomass was yielded during the process.

FIG. 17 (table 5) shows an analysis of the fungal biomass harvested from this experiment after washing of the biomass to extract the yeast residues and the feed-stock residues.

Experiment 4

Ethanol and Fungal Biomass Production from Thin Stillage in Industrial Process

Based on previous results, N. intermedia was examined in an industrial process bioreactor of 80 $m^3$. Inoculum was produced under aseptic conditions in a 26 L bioreactor and was then moved to the industrial bioreactor with a starting volume of 12.4 $m^3$ pasteurised thin stillage with 0.25 vvm aeration. After 5.4 g/L ethanol was produced, the bioreactor was further filled up to 27.6 $m^3$ which within 12 h resulted in production of 123 kg ethanol and 150 kg fungal biomass.

Experiment 5

Whole Stillage

Figure 1A:
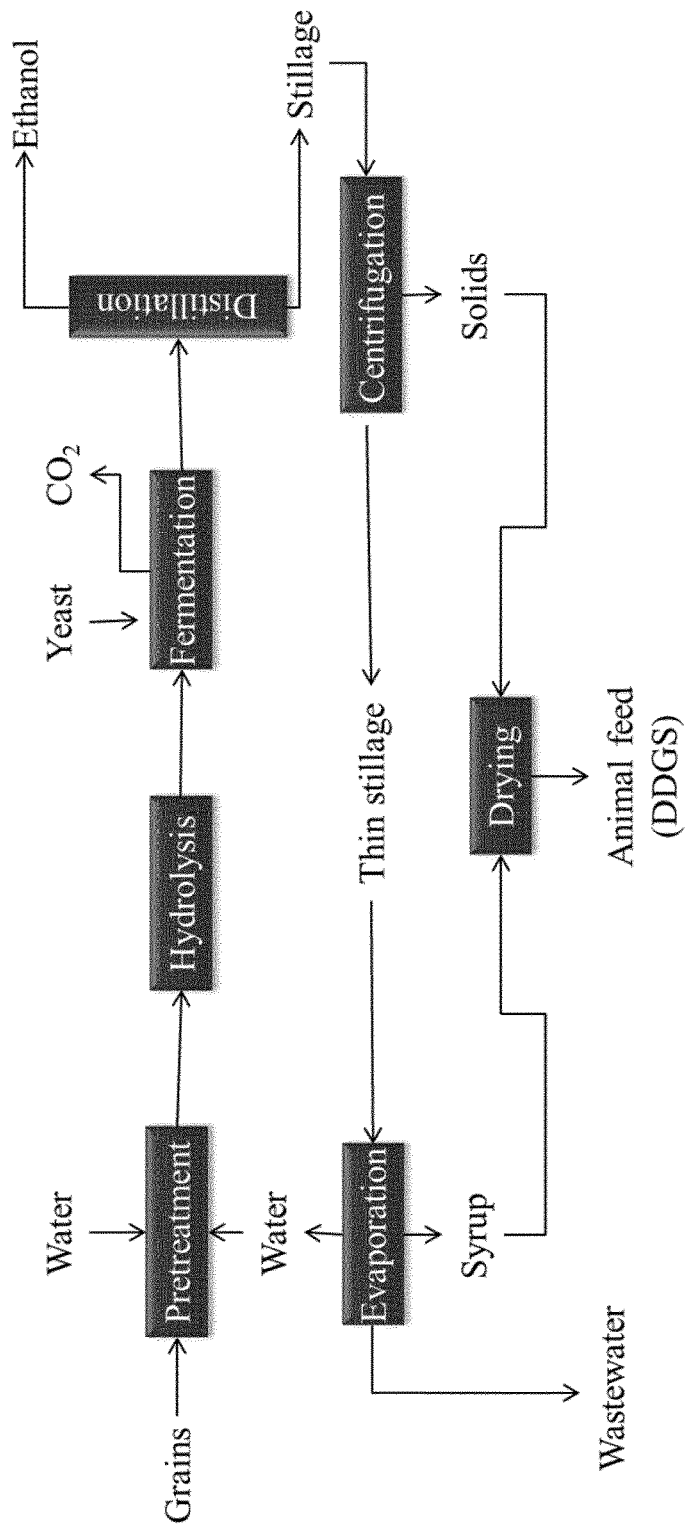
Figure 1B:
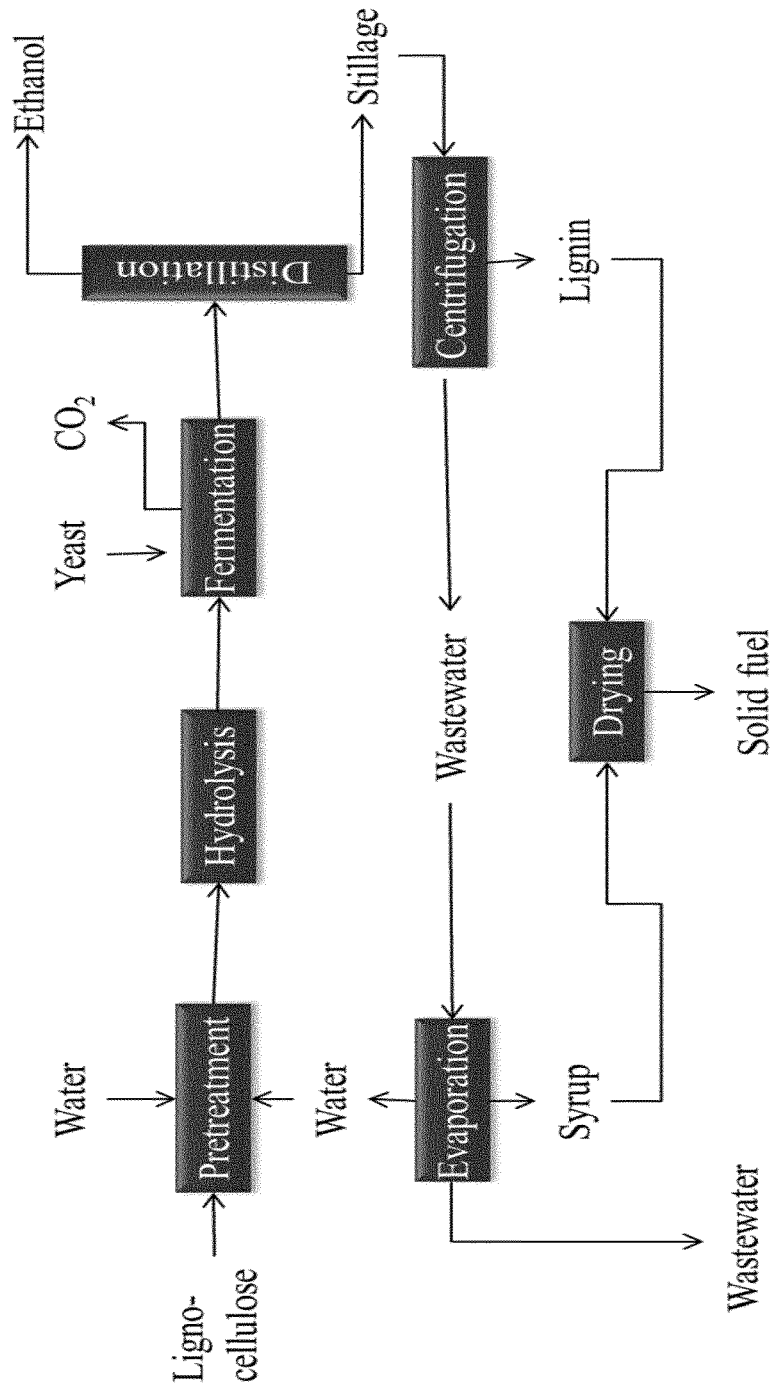
Figure 2A:
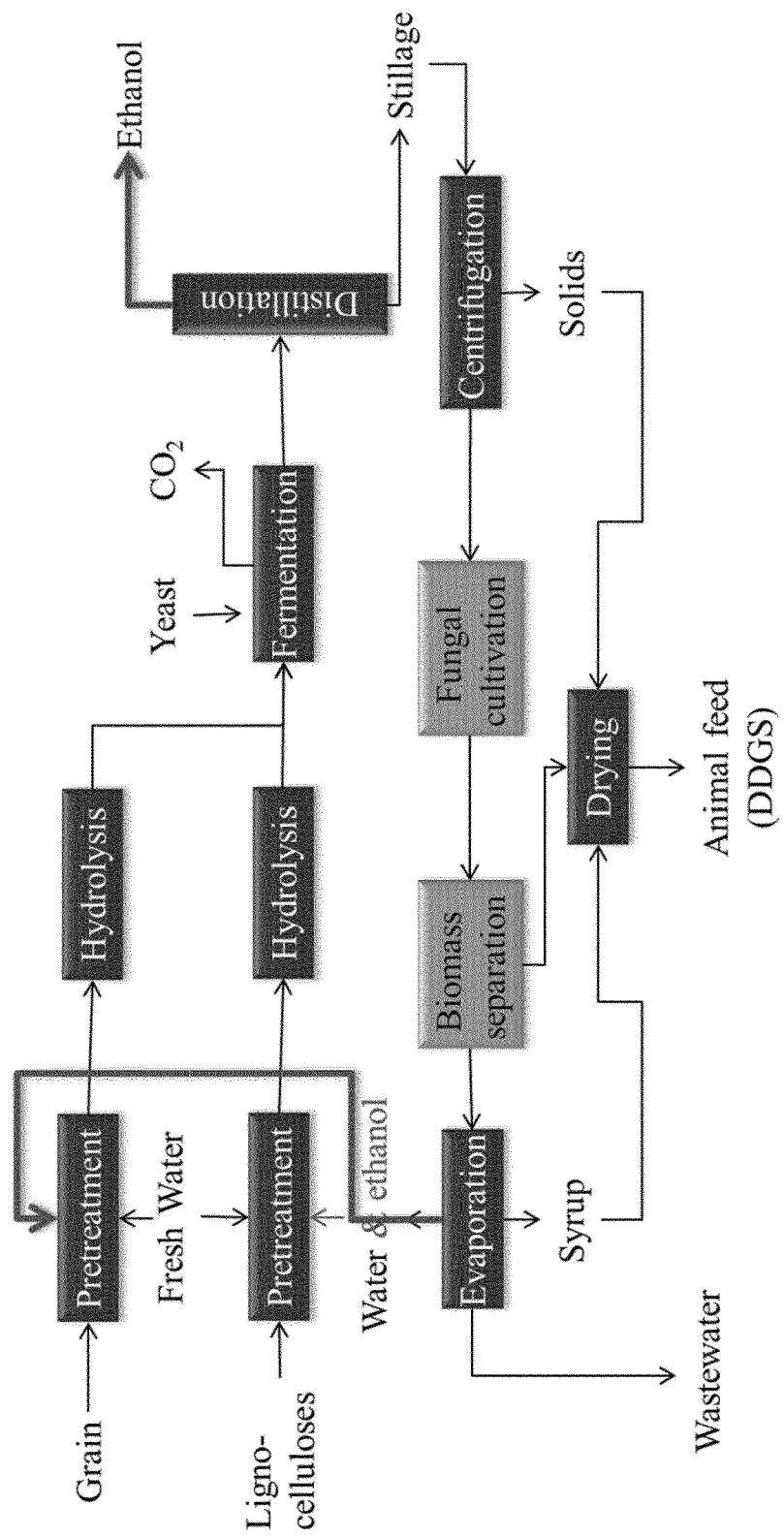
Figure 2B:
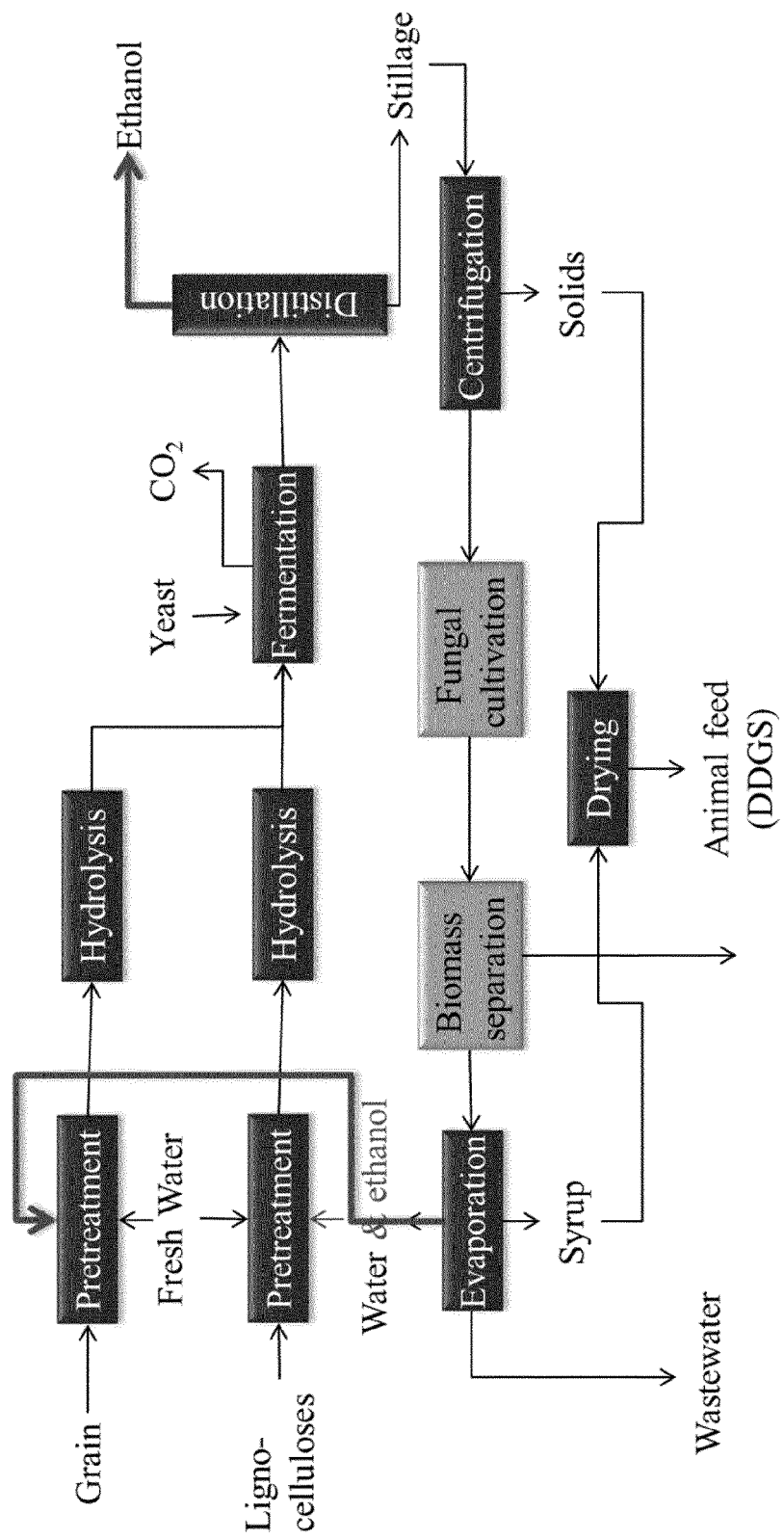
Figure 2C:
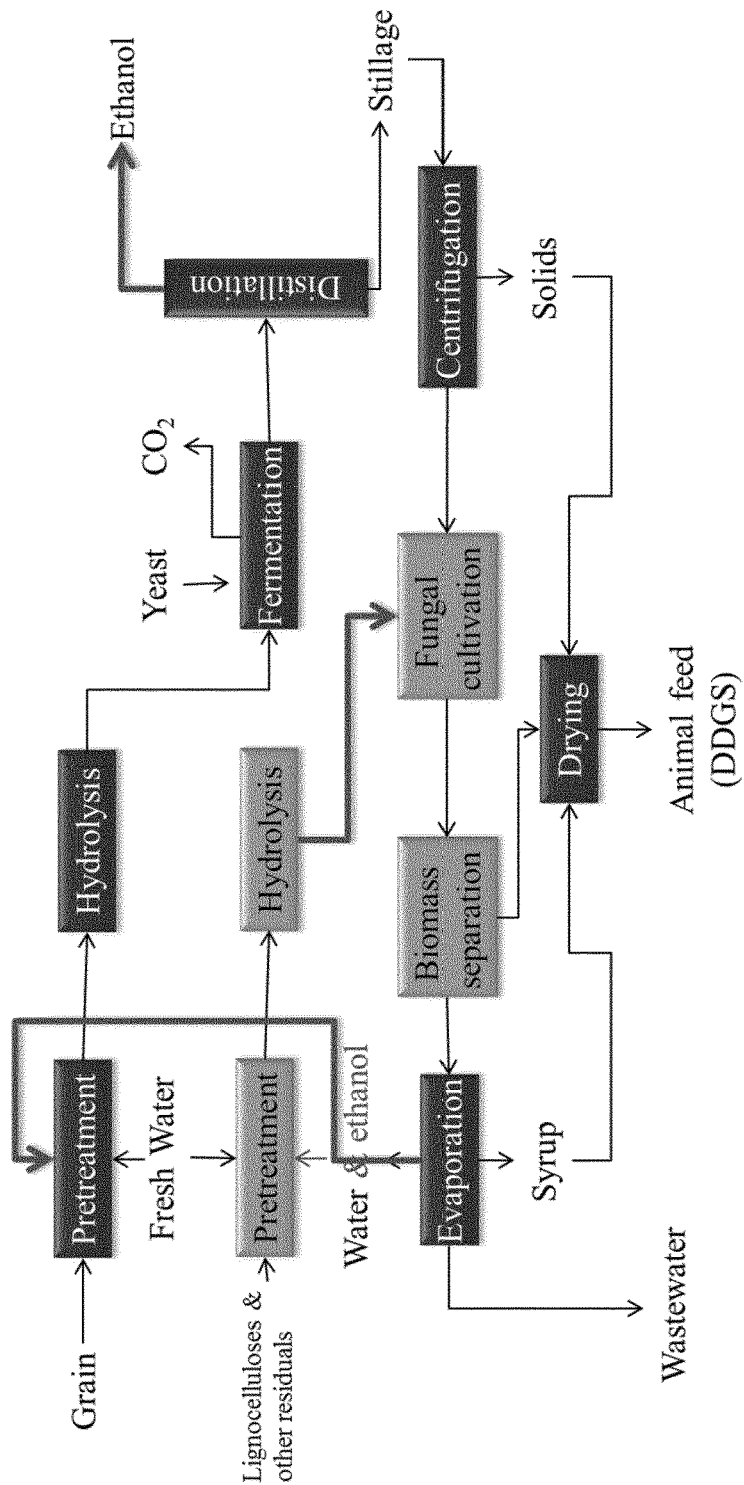
Figure 2D:
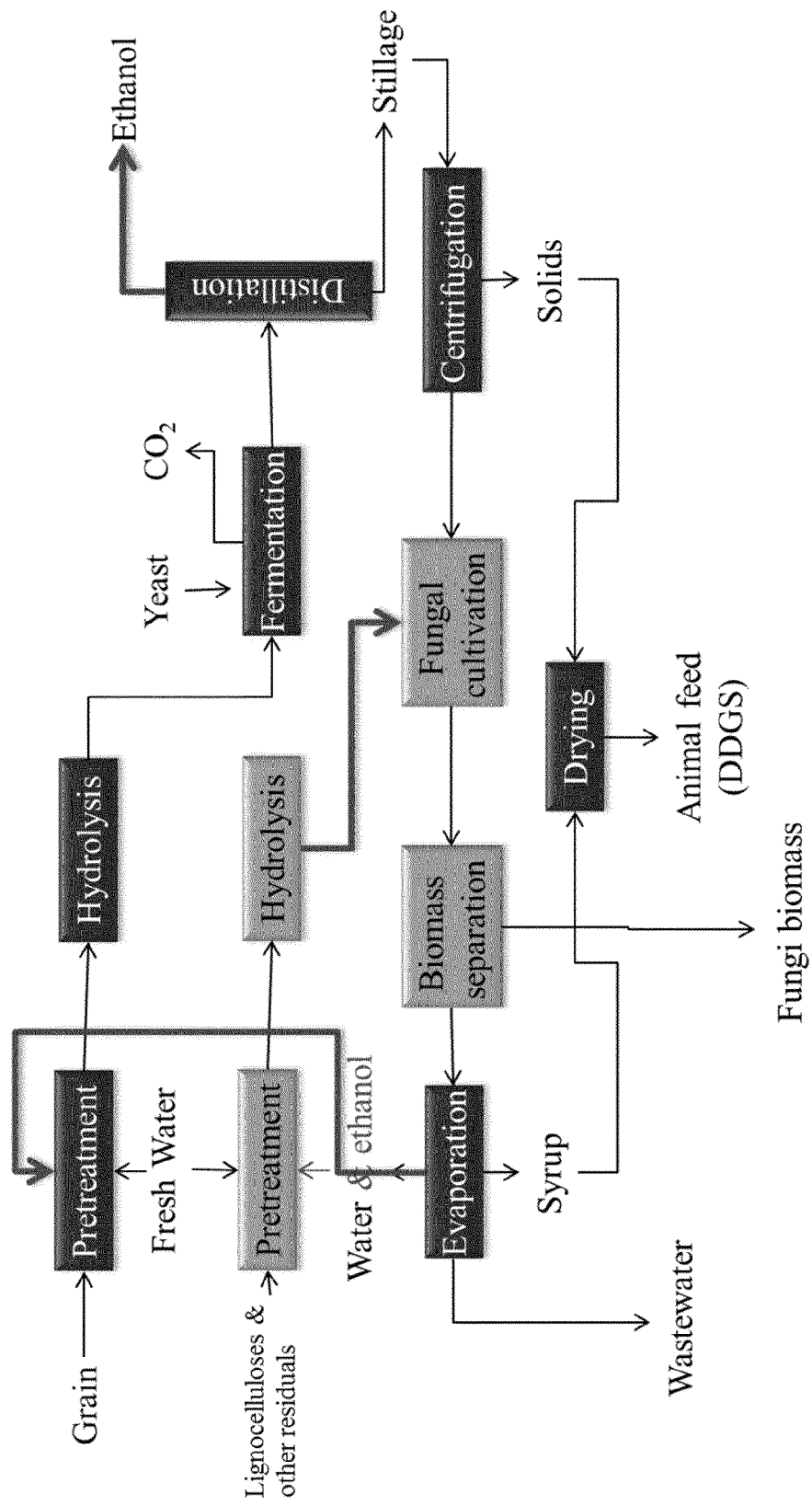
Figure 3:
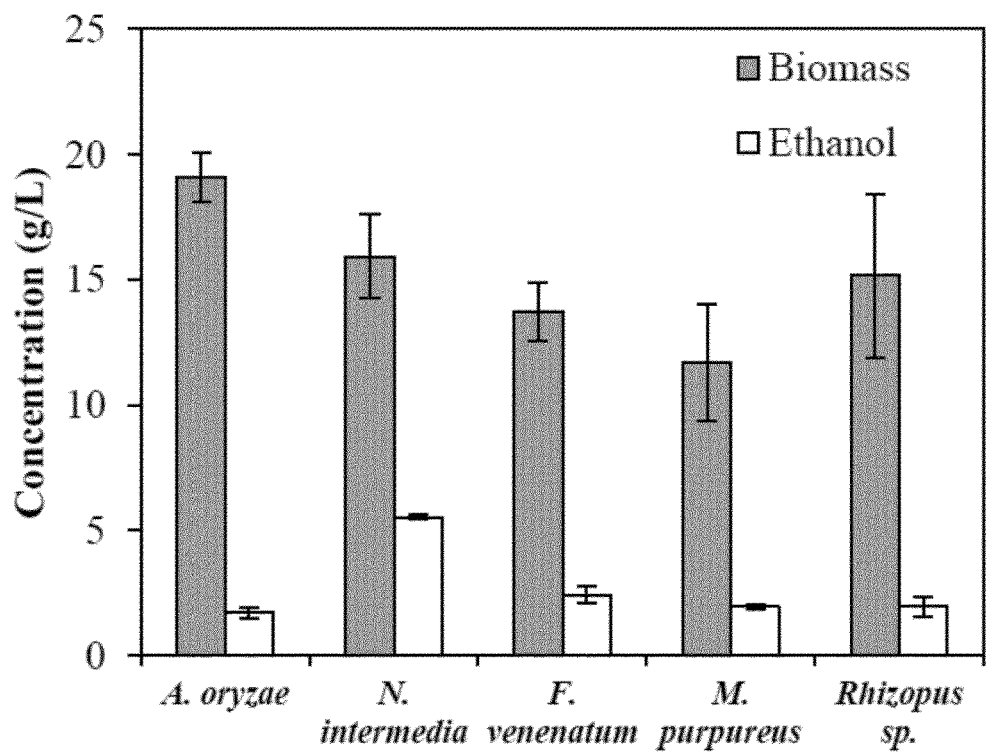
Figure 4:
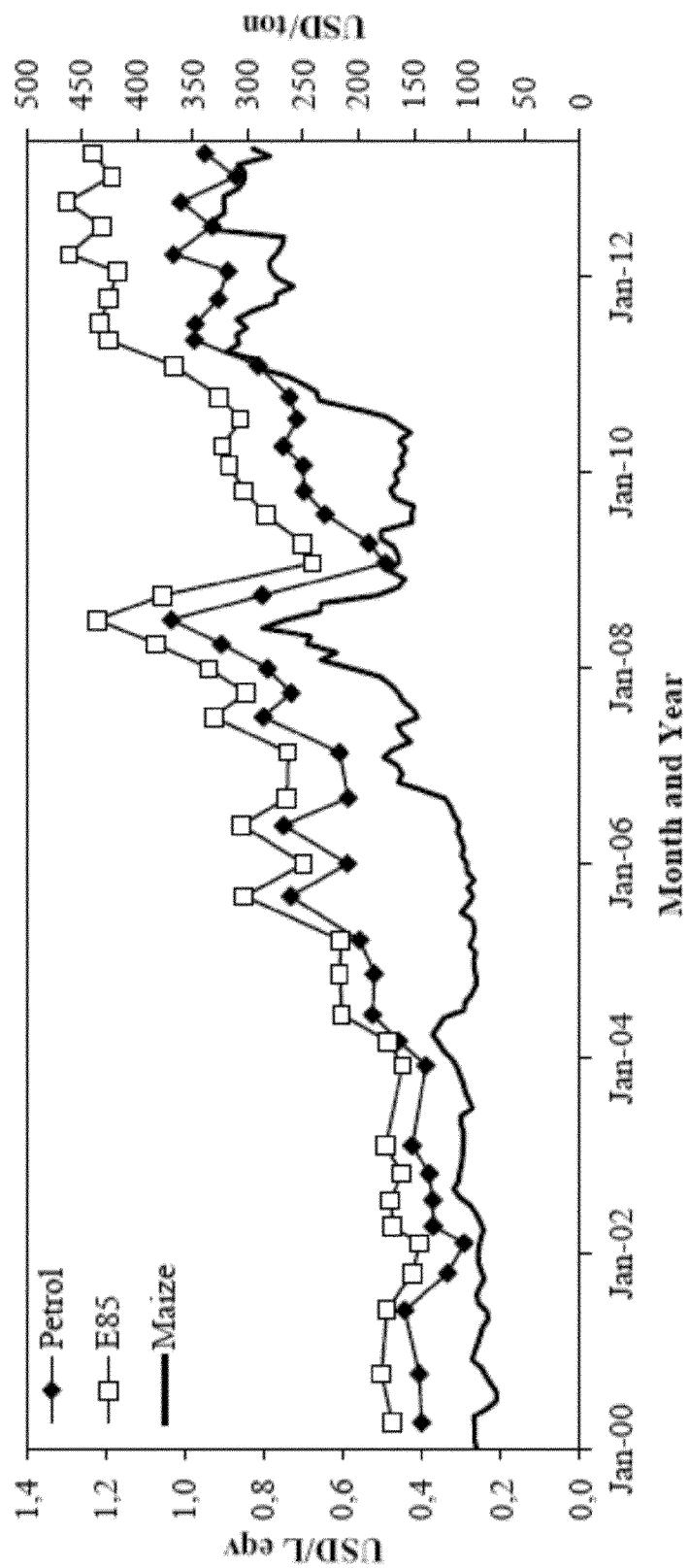
Figure 5:
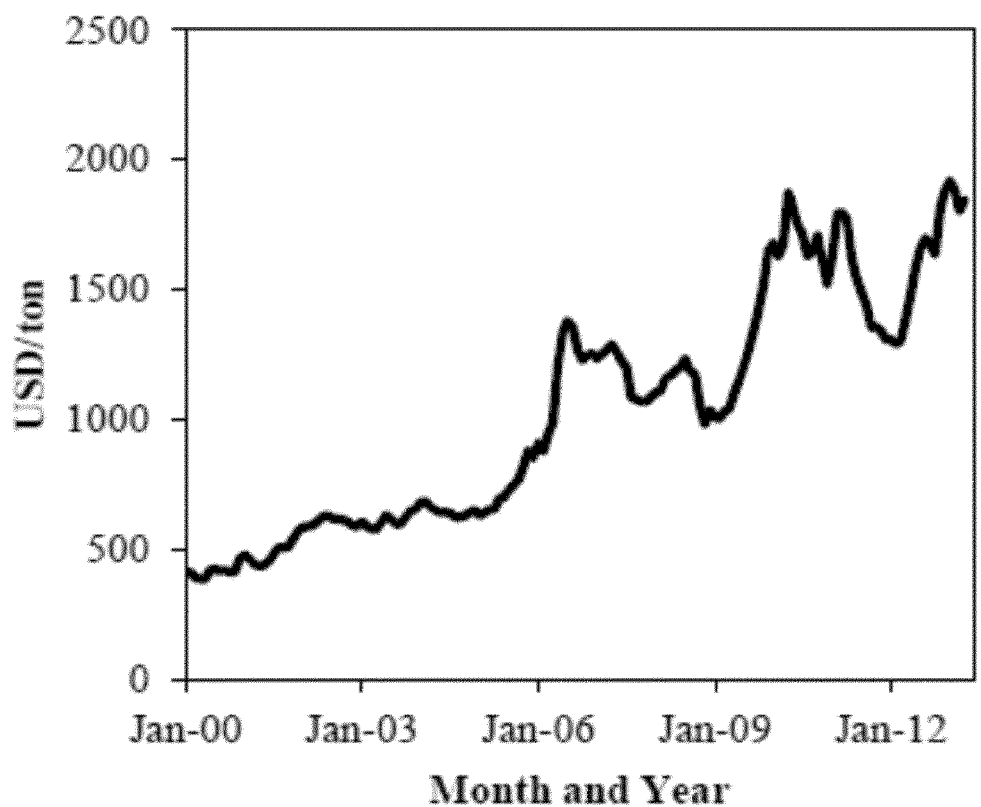
Figure 8:
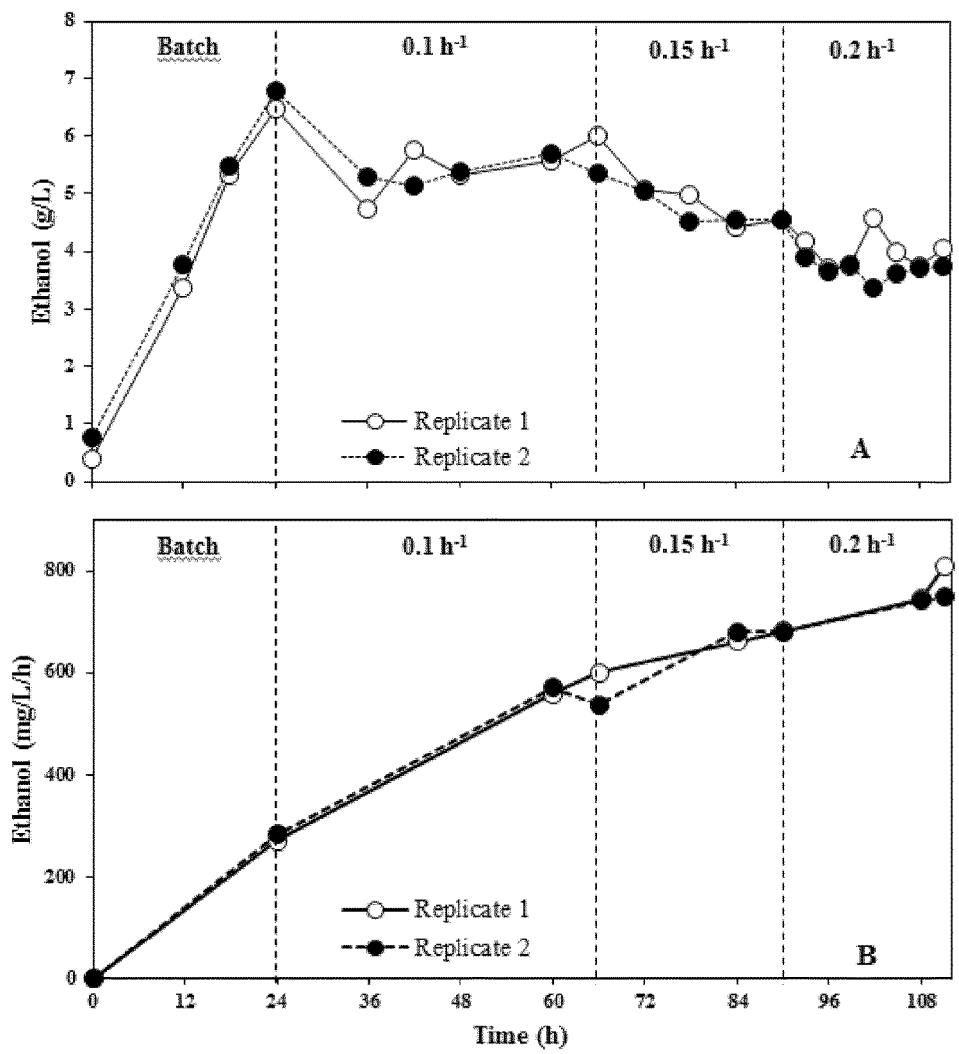
Figure 11:
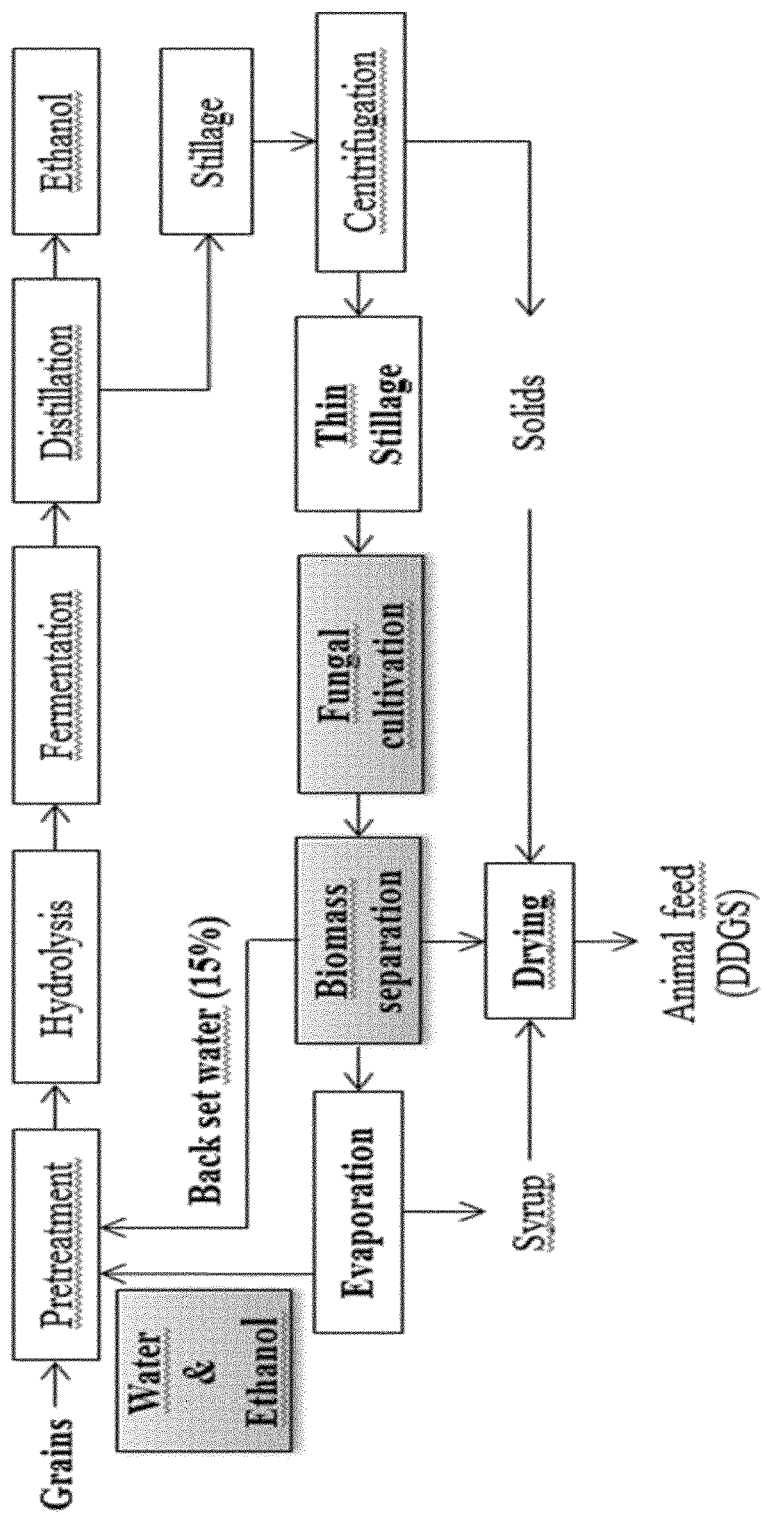
Figure 12:
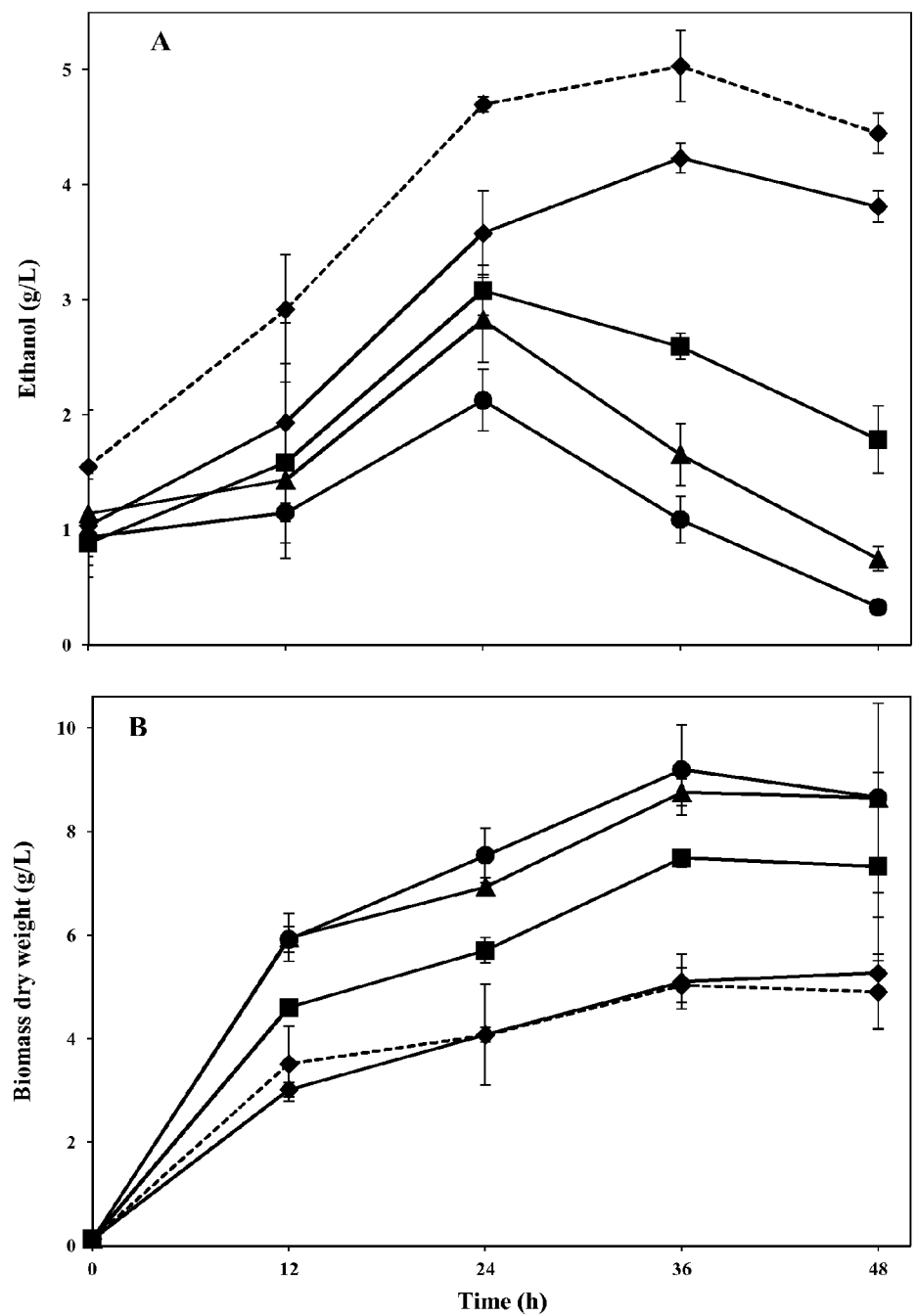
Figure 13:
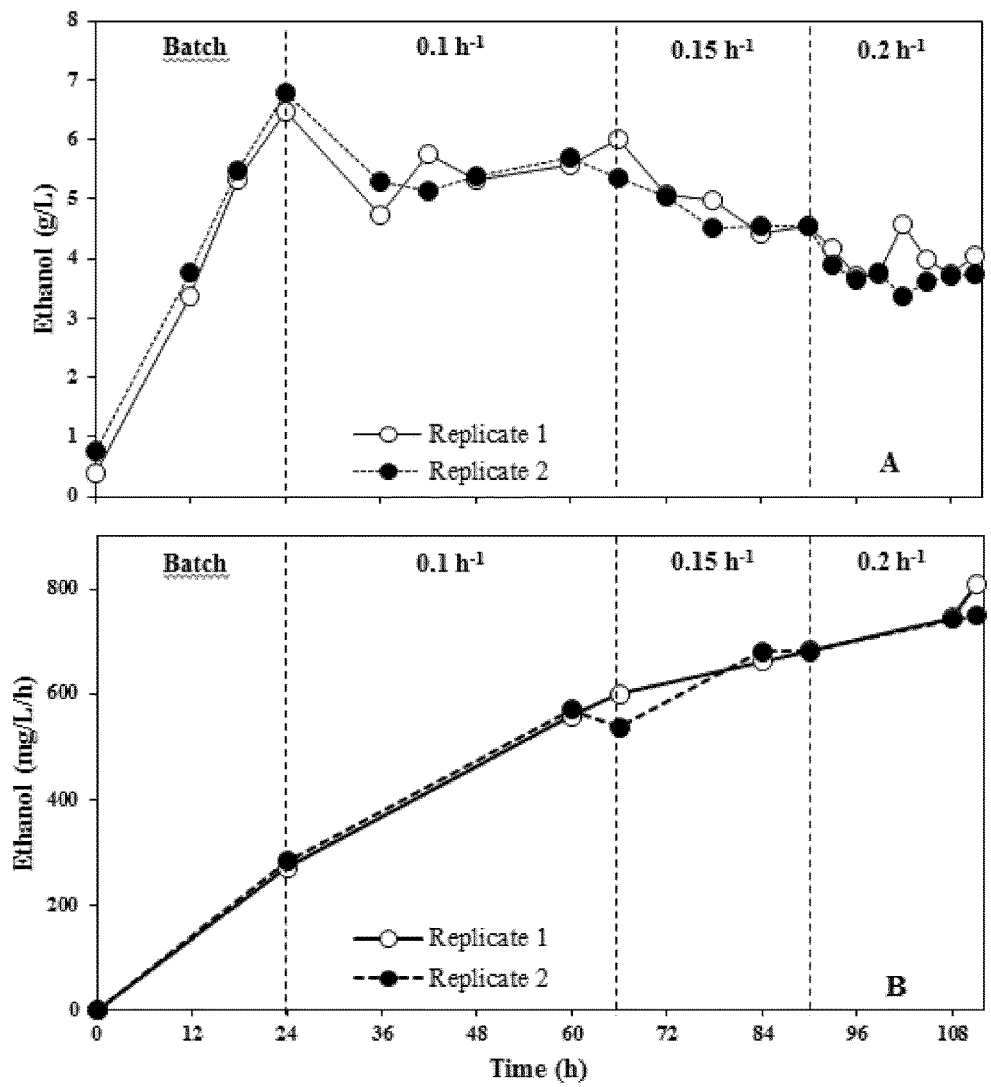
Figure 14:
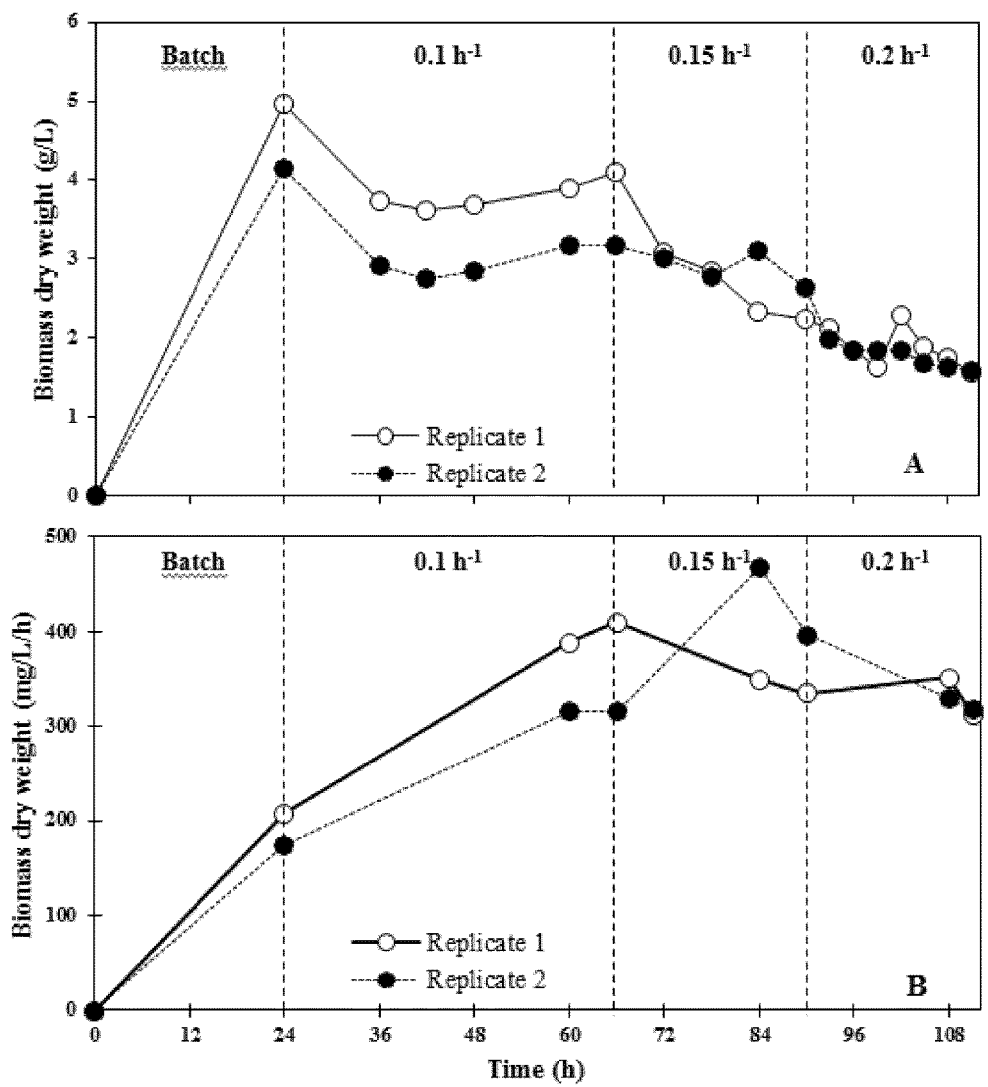
Figure 15:
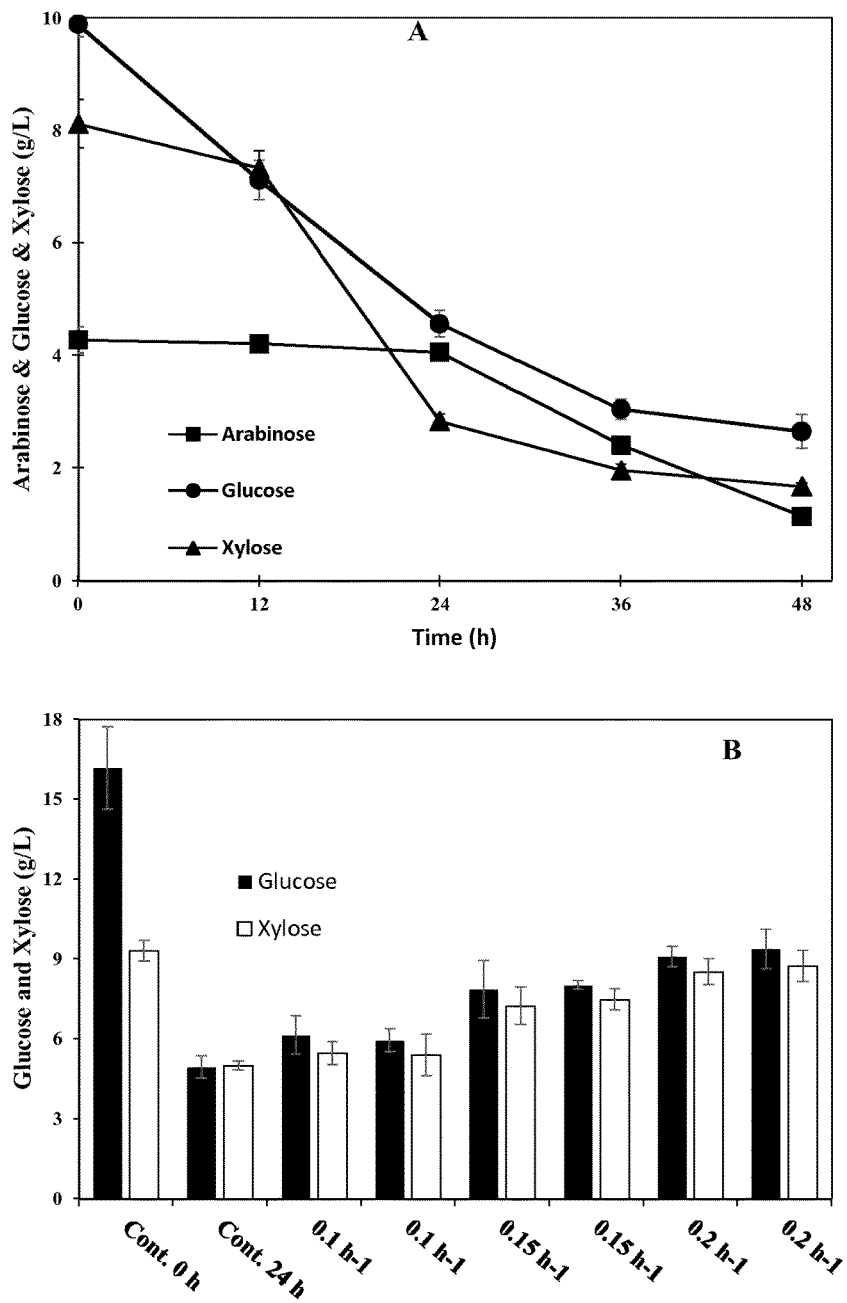
Figure 16:
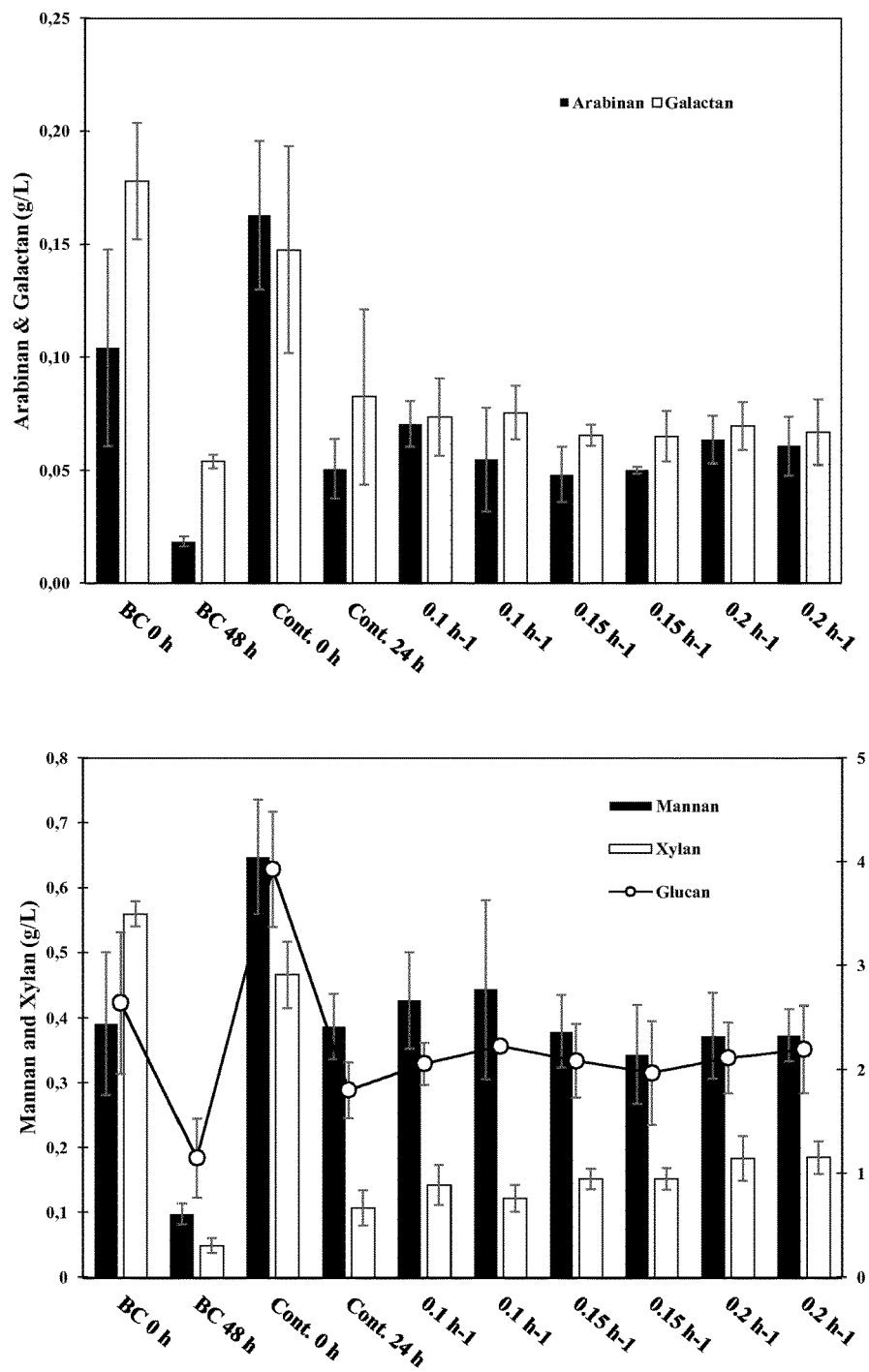
Figure 18:
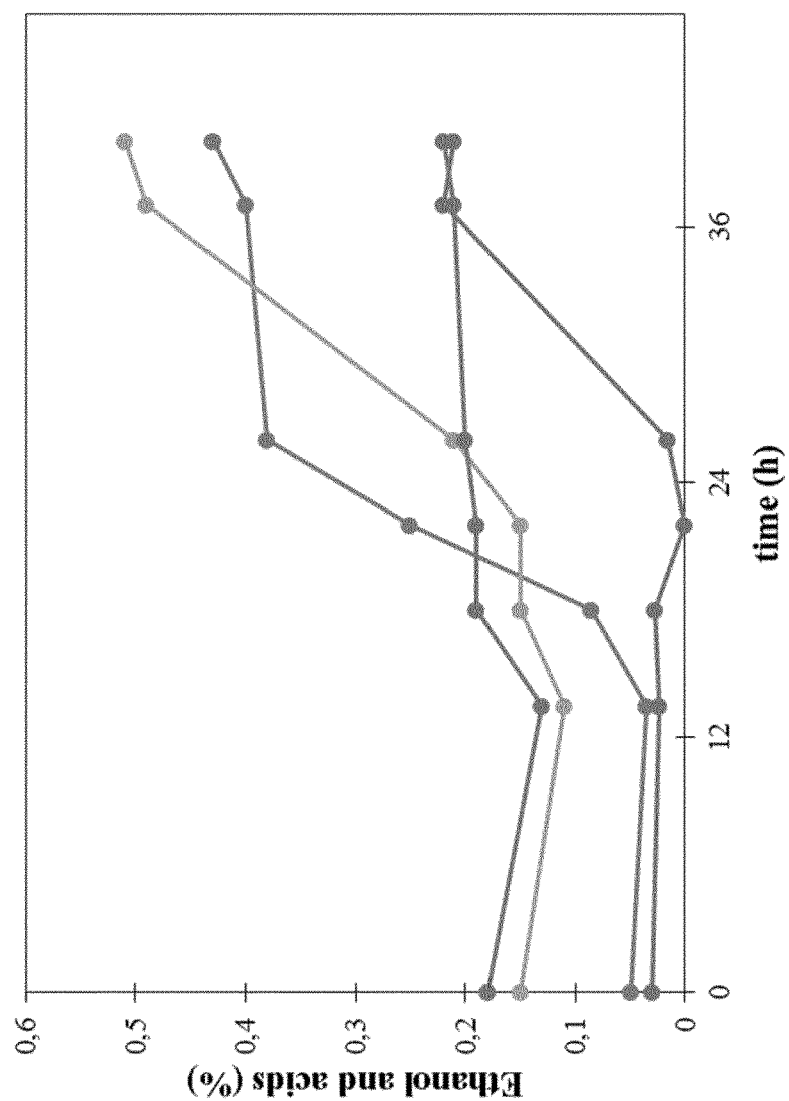
FIG. 18 shows profiles of ethanol and contamination-derived acids during cultivation of Neurospora intermedia in 20 $m^3$ thin stillage.
Figure 19:
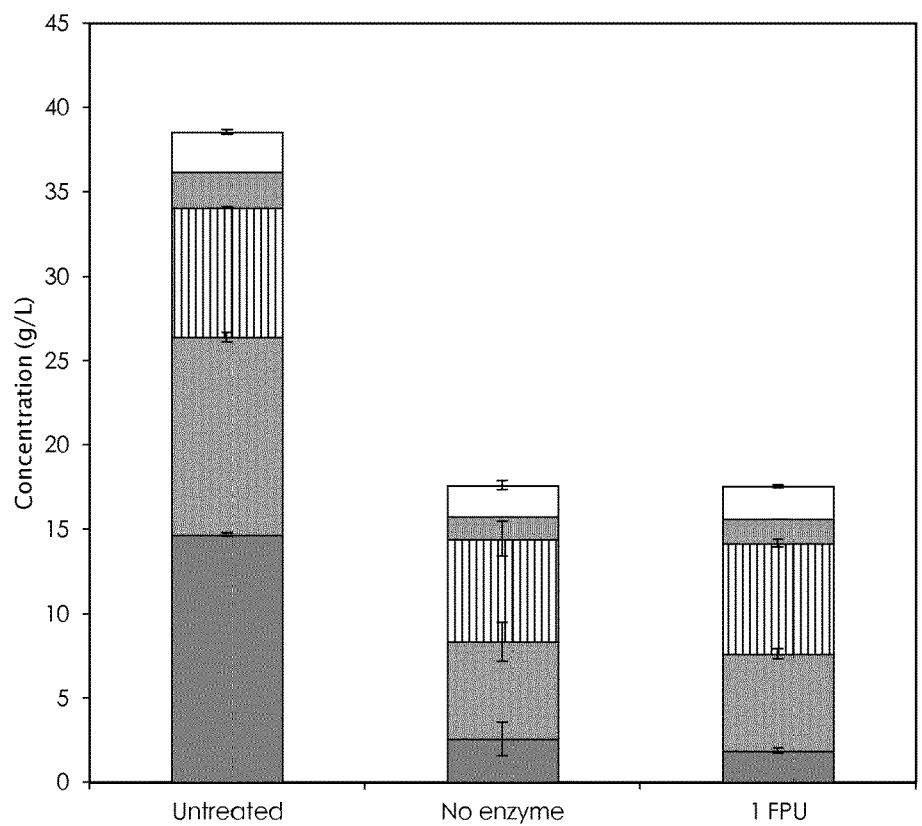
Figure 20:
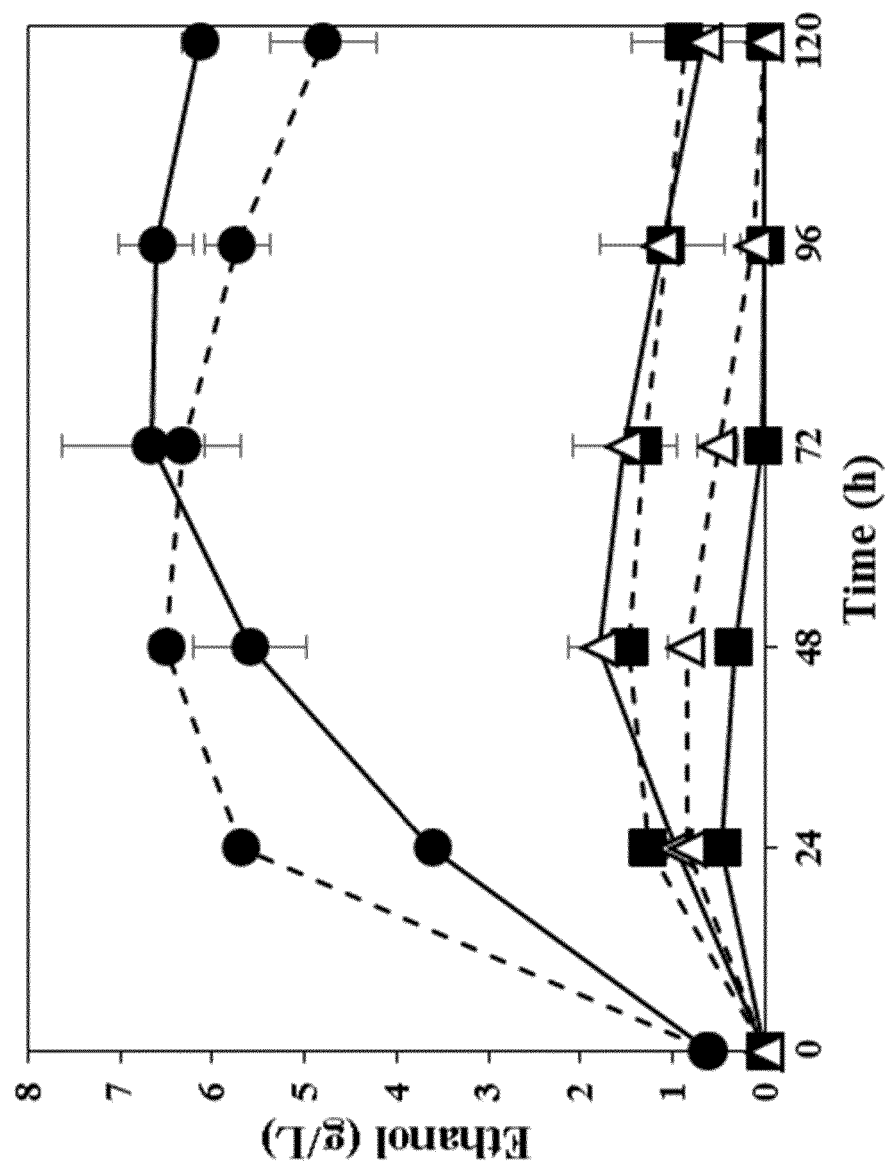

Compared with thin stillage, whole stillage has a theoretically higher potential for ethanol production due to the higher solid content. Cultivation of N. intermedia on whole stillage in shake flasks resulted in production of 5.3 g/L ethanol. As whole stillage contain an appreciate amount of cellulose, by supplementing the stillage with 1, 5, and 10 FPU cellulase/g suspended solids, the ethanol production could be improved to 8.6, 10.5, and 11.6 g/L, respectively. When investigated separately, the larger solids in whole stillage which are not present in thin stillage, could be used to produce ca 1 g/L additional ethanol by cultivation with N. intermedia and addition of cellulase. Analysis of the solids and dissolved carbohydrates also revealed that the addition of enzymes had the largest effect on the suspended solids, while the dissolved carbohydrates were only broken down faster in the presence of enzymes and reached the same end-point without enzyme addition (FIGS. 19 & 20).

Experiment 6

Pretreated Wheat Bran

Figure 21:
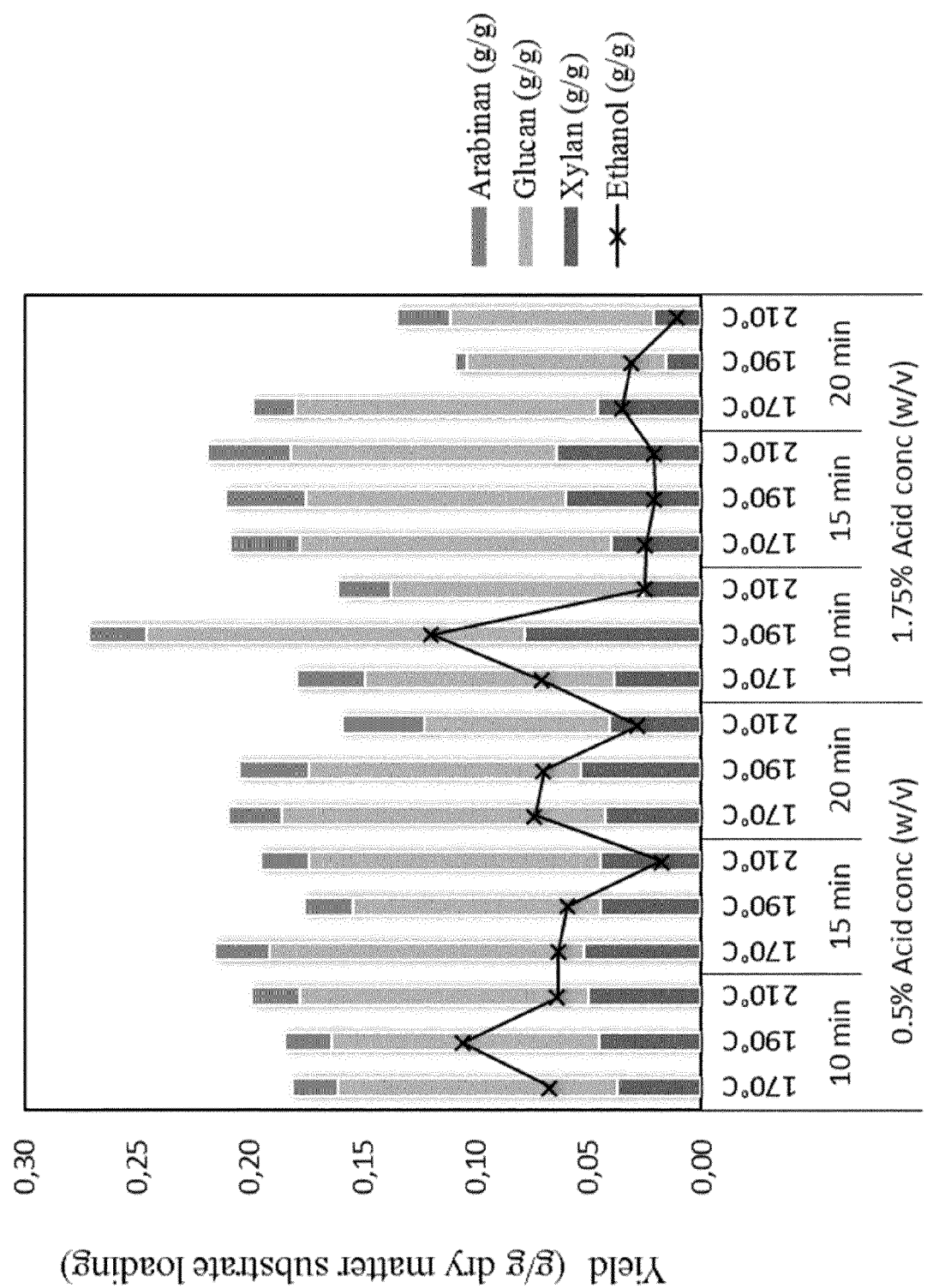

A lignocellulosic material closely associated with wheat flour production is wheat bran, which is the hard outer layer of the wheat grain traditionally removed during the milling process. In an experiment, wheat bran was pretreated with dilute phosphoric acid with concentration of 0.5-3.0 w/v, temperature 150-210° C., and pretreatment time 5-20 minutes in bench reactors. The pretreated bran was then hydrolysed using cellulose and fermented using N. intermedia. Optimum pretreatment conditions were identified at >1.75% w/v phosphoric acid, 190° C. for 10 min, leading to 85% of the theoretical ethanol yield based on hexose content of the bran. The results are summarized in FIGS. 21 and 23.

In another trial, the pretreatment of wheat bran was carried out using a continuous counter current industrial pretreatment process (SEKAB, Ö-vik, Sweden), followed by enzymatic hydrolysis and fermentation by N. intermedia. The result indicates 95% of the theoretical ethanol yield, based on hexose content of the bran.

Experiment 7

Pretreated Wheat Straw

Figure 22:
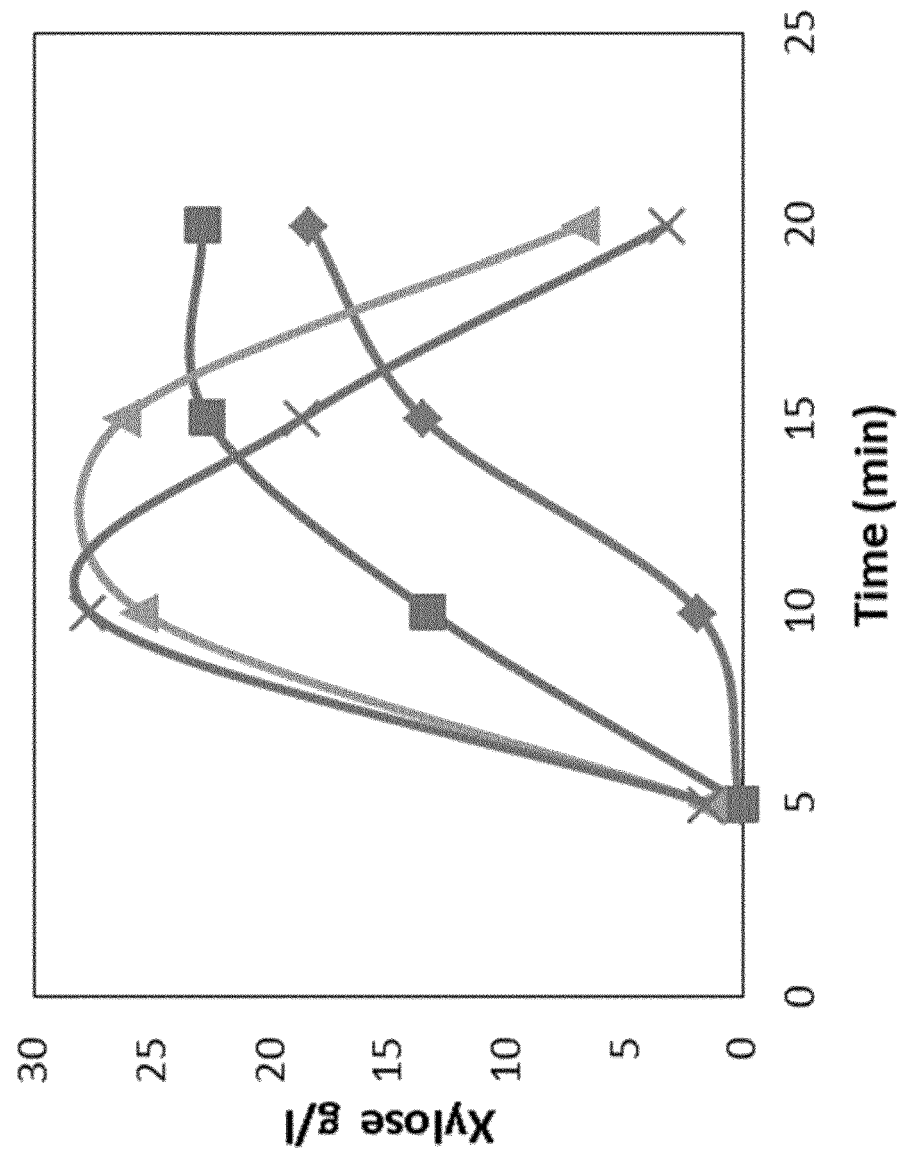
Figure 23:
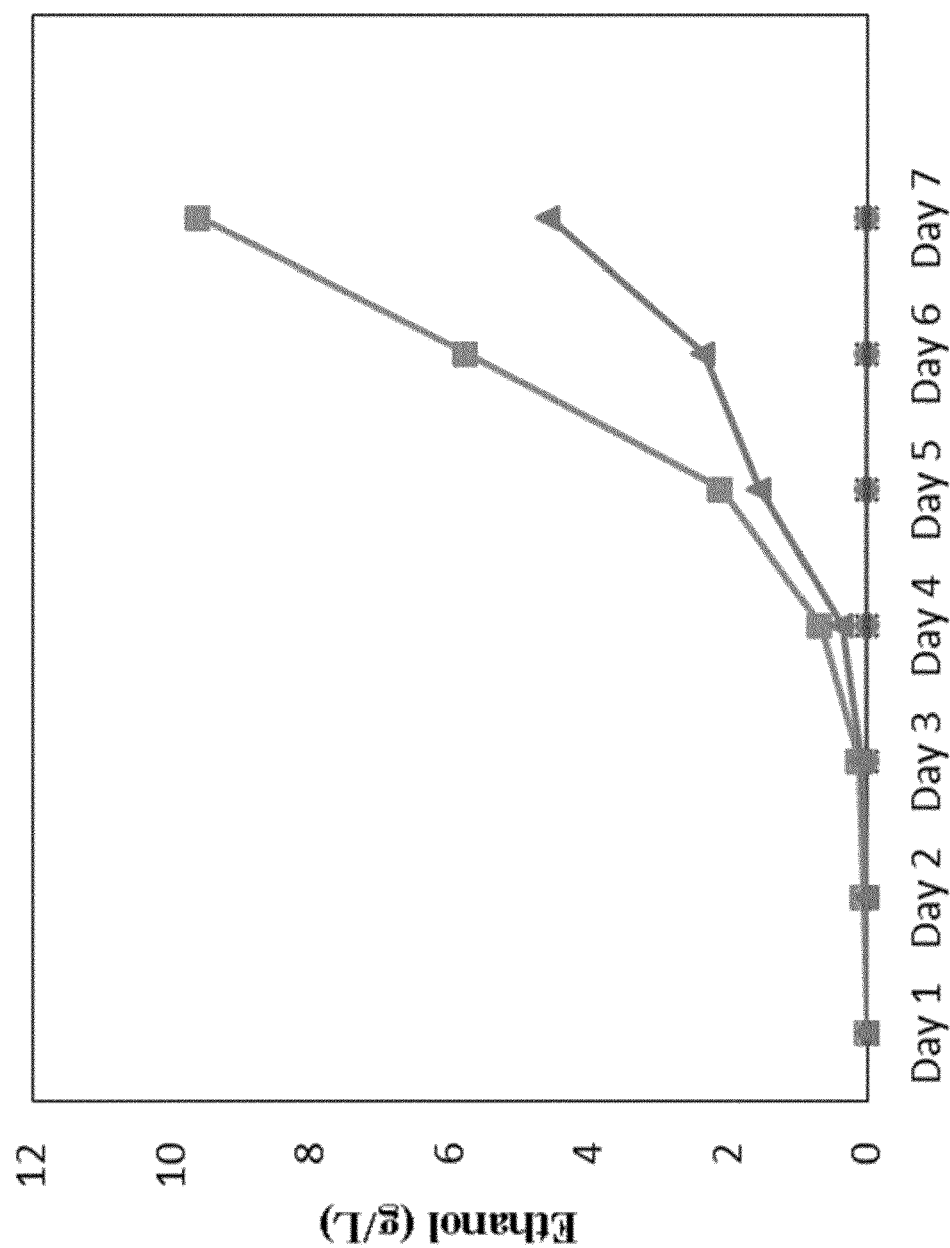

Another lignocellulosic material wide available is wheat straw. The straw was pretreated with varying phosphoric acid concentrations (0.5-3.0 w/v), temperature (150-210° C.), and pretreatment time (5-20 minutes) in bench reactors. Optimum pretreatment conditions were identified at 1.75% w/v phosphoric acid, 190° C. for 10 min. A good indicator of the effect of dilute acid pretreatment is the release of hemicellulose monomers released during pretreatment, in this case xylose (FIGS. 22 and 23).

REFERENCES

1. Alternative fuels data center. 2013. *Alternative fuel price report*, U.S. Department of Energy
2. Ferreira, J. A., Lennartsson, P. R., Edebo, L., Taherzadeh, M. J. 2013a. *Zygomycetes-based biorefinery: Present status and future prospects. Bioresource Technology*, 135, 523-532.
3. Ferreira, J. A., Lennartsson, P. R., Taherzadeh, M. J. 2013b. *Valorisation of thin stillage using food-grade Zygomycetes and Ascomycetes filamentous fungi*. Manuscript.
4. Gibbs, P. A., Seviour, R. J., Schmid, F. 2000. *Growth of filamentous fungi in submerged culture: Problems and possible solutions. Critical Reviews in Biotechnology*, 20(1), 17-48.
5. IEA. 2012. *Key world energy statistics*. International Energy Agency, Paris.

6. Kaye-Blake, W. 2010. *Biofuel and food: it's complicated.* Biofuels, 1(4), 511-514.
7. Nyman, J., Lacintra, M. G., Westman, J. O., Berglin, M., Lundin, M., Lennartsson, P. R., Taherzadeh, M. J. 2013. *Pellet formation of zygomycetes and immobilization of yeast.* New Biotechnology 30(5), 516-522.
8. REN21. 2012. *Renewables 2012 global status report.* REN21 Secretariat, Paris.
9. Taherzadeh, M. J., Karimi, K. 2008. *Pretreatment of lignocellulosic wastes to improve ethanol and biogas production: A review.* International Journal of Molecular Sciences, 9(9), 1621-1651.
10. Taherzadeh, M. J., Lennartsson, P. R., Teichert, O., Nordholm, H. 2013. *Bioethanol production processes. in: Biofuels production,* (Eds.) V. Babu, A. Thapliyal, G. K. Patel, Scrivener publishing. Beverly, Mass.
11. The World Bank. 2013. *World databank, Glocal Economic Monitor (GEM) Commodities,* World Bank Group
12. Zelinski, T., Hauer, B. 2002. *Industrial biotransformations with fungi. in: The Mycota X: Industrial*
13. Taherzadeh, M. J., Lennartsson, P. R., Teichert, O., Nordholm, H., *Bioethanol production processes, Biofuels Production,* John Wiley & Sons, Inc. 2013, pp. 211-253.
14. Ferreira, J. A., Lennartsson, P. R., Taherzadeh, M. J., *Production of ethanol and biomass from thin stillage using food-Grade Zygomycetes and Ascomycetes filamentous fungi.* Energies 2014, 7, 3872-3885.
15. Gibbs, P. A., Seviour, R. J., Schmid, F., *Growth of filamentous fungi in submerged culture: Problems and possible solutions.* Critical Reviews in Biotechnology 2000, 20, 17-48.
16. Sastraatmadja, D. D., Tomita, F., Kasai, T., *Production of high-quality oncom, a traditional Indonesian fermented food, by the inoculation with selected mold strains in the form of pure culture and solid inoculum.* J. Grad. Sch. Agric. Hokkaido Univ. 2002, 70, 111-127.
17. Lennartsson, P. R., Erlandsson, P., Taherzadeh, M. J., *Integration of the first and second generation bioethanol processes and the importance of by-products.* Bioresource Technology 2014.
18. Millati, R., Edebo, L., Taherzadeh, M. J., *Performance of Rhizopus, Rhizomucor, and Mucor in ethanol production from glucose, xylose, and wood hydrolyzates.* Enzyme Microb. Tech. 2005, 36, 294-300.
19. Zamani, A., Taherzadeh, M. J., *Production of low molecular weight chitosan by hot dilute sulfuric acid.* Bioresources 2010, 5, 1554-1564.
20. NREL, *Preparation of samples for compositional analysis,* U.S. Department of Energy, Colorado, USA 2008a.
21. NREL, *Structural carbohydrates and lignin in biomass,* U.S. Department of Energy, Colorado, USA 2011.
22. NREL, *Determination of total solids in biomass and total dissolved solids in liquid process samples,* U.S. Department of Energy, Colorado, USA 2008b.
23. NREL, *Determination of sugars, by-products and degradation products in liquid fraction samples,* U.S. Department of Energy, Colorado, USA 2008c.
24. Wall, J. S., Bothast, R. J., Lagoda, A. A., Sexson, K. R., Wu, Y. V., *Effect of recycling distillers' solubles on alcohol and feed production from corn fermentation.* J. Agr. Food Chem. 1983, 31, 770-775.
25. Ferreira, J. A., Lennartsson, P. R., Niklasson, C., Lundin, M., et al., *Spent sulphite liquor for cultivation of an edible Rhizopus sp.* Bioresources 2012, 7, 173-188.
26. Bartnicki-Garcia, S., *Cell wall, chemistry, morphogenesis, and taxonomy of fungi.* Annu. Rev. Microbiol. 1968, 22, 87-108.
27. Hu, K.-J., Hu, J.-L., Ho, K.-P., Yeung, K.-W, *Screening of fungi for chitosan producers, and copper adsorption capacity of fungal chitosan and chitosanaceous materials.* Carbohyd. Polym. 2004, 58, 45-52.
28. Gonzalez, R., Campbell, P., Wong, M., *Production of ethanol from thin stillage by metabolically engineered Escherichia coli.* Biotechnol. Lett. 2010, 32, 405-411.

The invention claimed is:

1. A process for producing bioethanol and a fungal biomass, comprising
    carrying out a first generation bioethanol process which comprises fermenting starch- or sugar-based raw materials with yeast to produce ethanol and stillage; and
    integrating a second generation bioethanol process into the first generation bioethanol process;
    wherein the second generation process comprises cultivating filamentous fungi selected from the group consisting of food-related strains of Ascomycetes on whole stillage and/or thin stillage from the first generation process,
    wherein the second generation process produces ethanol and fungal biomass.

2. The process of claim 1, wherein the filamentous fungi are selected from the group consisting of *Rhizopus* sp.; *Fusarium* venenatium; *Aspergillus oryzae*; *Monascus purpureus*, *Neurospora intermedia* and combinations thereof.

3. The process of claim 2, wherein the filamentous fungi are *Neurospora intermedia*.

4. The process of claim 1, wherein the integrated second generation process yields an at least 2.5% improvement of ethanol production compared to the ethanol production of the first generation bioethanol process into which the second generation bioethanol process is integrated.

5. The process of claim 1, wherein the integrated second generation process yields 1-20% improvement of ethanol production, compared to the ethanol production of the first generation bioethanol process into which the second generation bioethanol process is integrated.

6. The process of claim 1, wherein the integrated second generation process produced 1-30 g/L fungal biomass and 1-50 g/L ethanol from the thin stillage, from the whole stillage, or from the thin stillage and the whole stillage.

7. The process of claim 1, wherein the integrated second generation process produces 1-20 g/L fungal biomass and 1-5 g/L ethanol from the thin stillage, from the whole stillage, or from the thin stillage and the whole stillage.

8. The process of claim 1, wherein said starch- or sugar-based raw material comprises wheat.

9. The process of claim 1, wherein the starch- or sugar-based raw materials comprise lignocellulosic feed-stock.

10. The process of claim 9, wherein the lignocellulosic feed-stock is supplied into a dry mill.

11. The process of claim 9, wherein the lignocellulosic feed-stock is selected from the group consisting of corn stover, wheat straw, switch grass and combinations thereof.

12. The process of claim 1, wherein the fungal cultivation step takes place in an airlift reactor and/or bubble column.

* * * * *